United States Patent
Hong

(10) Patent No.: US 11,794,074 B2
(45) Date of Patent: Oct. 24, 2023

(54) APPARATUS AND METHOD FOR EXERCISE TYPE RECOGNITION

(71) Applicant: Dae-Geon Hong, Gyeonggi-do (KR)

(72) Inventor: Dae-Geon Hong, Gyeonggi-do (KR)

( * ) Notice: Subject to any disclaimer, the term of this patent is extended or adjusted under 35 U.S.C. 154(b) by 403 days.

(21) Appl. No.: 16/892,603

(22) Filed: Jun. 4, 2020

(65) Prior Publication Data

US 2020/0316433 A1 Oct. 8, 2020

Related U.S. Application Data

(60) Division of application No. 16/245,633, filed on Jan. 11, 2019, now abandoned, which is a continuation of
(Continued)

(30) Foreign Application Priority Data

Nov. 21, 2016 (KR) .................. 10-2016-0155013

(51) Int. Cl.
*A63B 24/00* (2006.01)
*A63B 23/14* (2006.01)
(Continued)

(52) U.S. Cl.
CPC .......... *A63B 24/0062* (2013.01); *A63B 21/00* (2013.01); *A63B 23/14* (2013.01);
(Continued)

(58) Field of Classification Search
None
See application file for complete search history.

(56) References Cited

U.S. PATENT DOCUMENTS

| 7,988,598 B2 * | 8/2011 | Trzecieski | G16H 40/67 |
| | | | 482/901 |
| 10,898,758 B2 * | 1/2021 | Bengtsson | A63B 24/0062 |

(Continued)

FOREIGN PATENT DOCUMENTS

| JP | 2004_184351 A | 7/2004 |
| JP | 2004_333279 A | 11/2004 |

(Continued)

*Primary Examiner* — Lina Cordero
(74) *Attorney, Agent, or Firm* — BACON&THOMAS,PLLC

(57) ABSTRACT

A method is provided. The method comprises a first step of acquiring wrist exercise information including at least one of orientation information and motion information of a wrist of a user, a second step of acquiring upper body exercise information including at least one of orientation information and motion information of a torso of the user, a third step of calculating, using reference wrist exercise information and reference upper body exercise information corresponding to each of a plurality of exercise types, a first similarity degree between the reference wrist exercise information and the wrist exercise information and a second similarity degree between the reference upper body exercise information and the upper body exercise information for each of the exercise types, and a fourth step of determining an actual exercise type performed by the user, among the exercise types, based on the first similarity degree and the second similarity degree.

12 Claims, 16 Drawing Sheets

Related U.S. Application Data application No. 16/051,633, filed on Aug. 1, 2018, now abandoned, which is a continuation of application No. PCT/KR2017/013157, filed on Nov. 20, 2017.

(51) Int. Cl.

| | | |
|---|---|---|
| *G06F 3/0346* | (2013.01) | |
| *G06F 3/01* | (2006.01) | |
| *G16H 20/30* | (2018.01) | |
| *G16H 40/63* | (2018.01) | |
| *A63B 21/00* | (2006.01) | |
| *A63B 71/06* | (2006.01) | |

(52) U.S. Cl.
CPC .......... *A63B 24/00* (2013.01); *A63B 24/0006* (2013.01); *A63B 24/0087* (2013.01); *A63B 71/06* (2013.01); *G06F 3/017* (2013.01); *G06F 3/0346* (2013.01); *G16H 20/30* (2018.01); *G16H 40/63* (2018.01); *A63B 2024/0012* (2013.01)

(56) References Cited

U.S. PATENT DOCUMENTS

| | | | |
|---|---|---|---|
| 2002/0086774 A1 | 7/2002 | Warner | |
| 2003/0013072 A1 | 1/2003 | Thomas | |
| 2003/0171189 A1 | 9/2003 | Kaufman | |
| 2006/0234842 A1* | 10/2006 | Minami | G01G 19/14 482/99 |
| 2007/0054786 A1* | 3/2007 | Piane, Jr. | A63B 21/00 482/94 |
| 2007/0293370 A1 | 12/2007 | Klinger | |
| 2008/0242512 A1* | 10/2008 | Kim | A63B 21/065 482/8 |
| 2011/0092337 A1 | 4/2011 | Srinivasan et al. | |
| 2011/0275480 A1 | 11/2011 | Champsaur | |
| 2012/0053014 A1* | 3/2012 | Zhu | A63B 21/4035 482/5 |
| 2012/0094804 A1* | 4/2012 | Bell | A63B 21/0083 482/99 |
| 2012/0183940 A1 | 7/2012 | Aragones et al. | |
| 2013/0190903 A1 | 7/2013 | Balakrishnan et al. | |
| 2014/0248996 A1* | 9/2014 | Adel | H04W 4/80 482/8 |
| 2014/0315689 A1* | 10/2014 | Vauquelin | A63B 22/0235 482/8 |
| 2016/0101320 A1 | 4/2016 | Tsutsui et al. | |
| 2016/0199693 A1 | 7/2016 | Vermilyea et al. | |
| 2016/0199697 A1* | 7/2016 | Orfield | A63B 21/151 482/8 |
| 2016/0263439 A1 | 9/2016 | Ackland | |
| 2017/0128765 A1* | 5/2017 | Garretson | G09B 19/0038 |
| 2019/0160335 A1* | 5/2019 | Bengtsson | A63B 21/0628 |

FOREIGN PATENT DOCUMENTS

| | | | |
|---|---|---|---|
| JP | 2007_236917 A | | 9/2007 |
| JP | 2011136131 A | * | 7/2011 |
| KR | 102016_0001958 A | | 1/2016 |
| KR | 102016_0054325 A | | 5/2016 |
| KR | 101675548 B1 | * | 11/2016 |

* cited by examiner

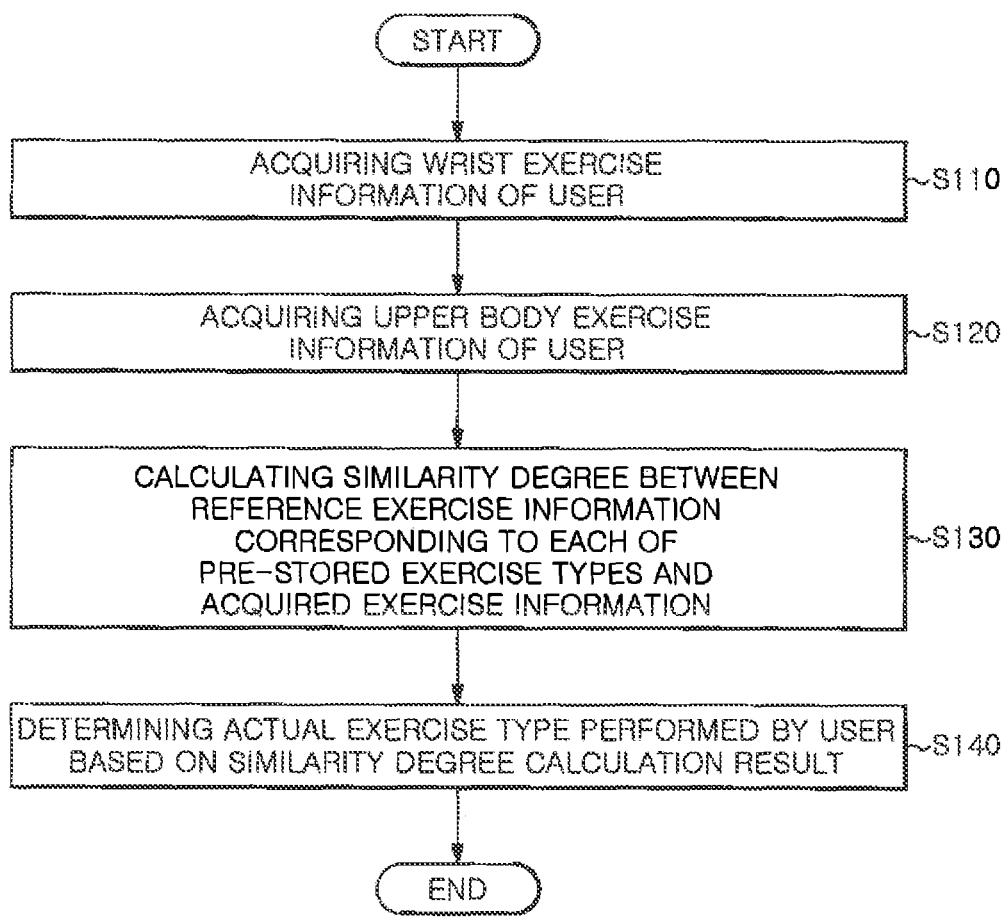

(A)　　　　　　　　(B)

(A)　　　　　　　　(B)

FIG.4D
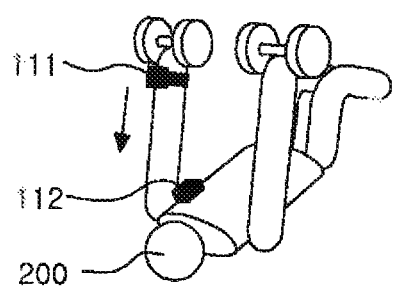
(A)
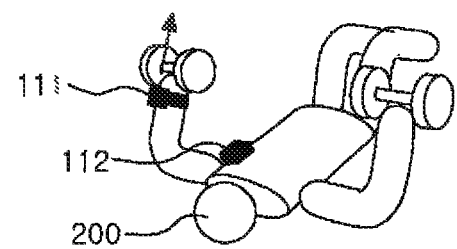
(B)
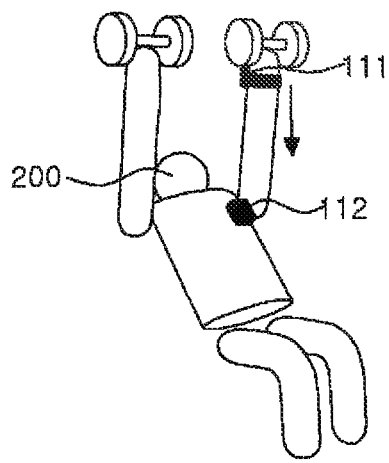
(C)
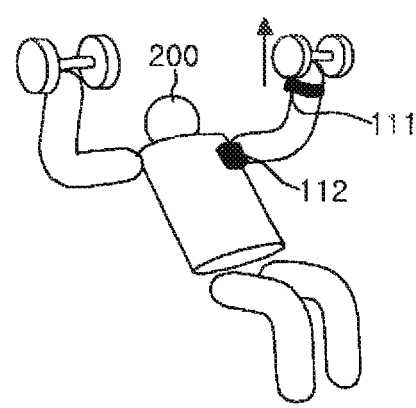
(D)

FIG. 4F
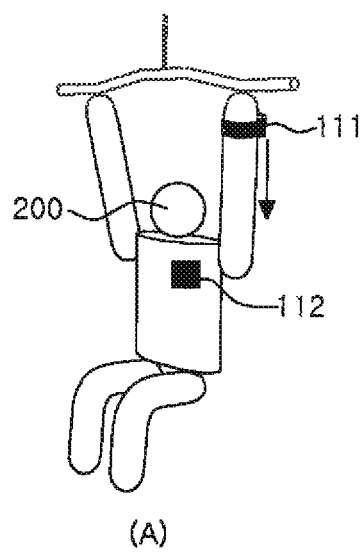
(A)
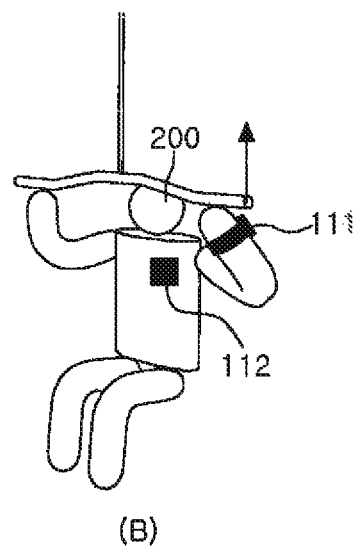
(B)
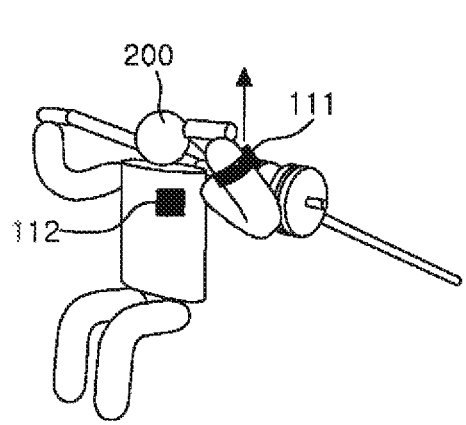
(C)
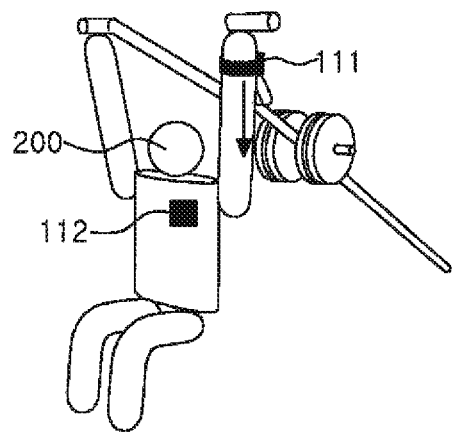
(D)

(A)  (B)

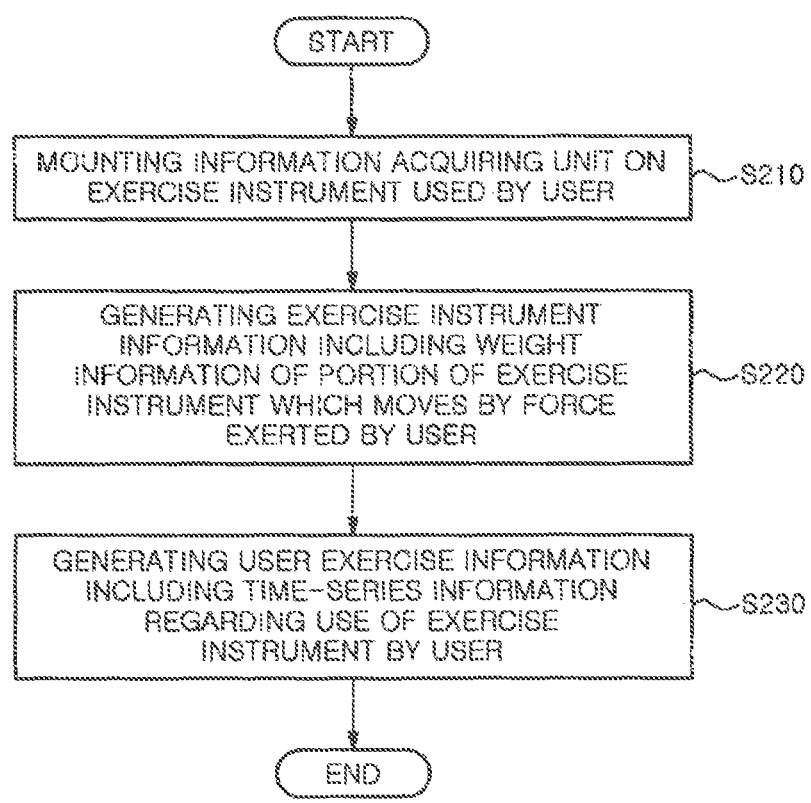

APPARATUS AND METHOD FOR EXERCISE TYPE RECOGNITION

CROSS-REFERENCE TO RELATED APPLICATIONS

The present application is a continuation of International Patent Application No. PCT/KR2017/013157, filed on Nov. 20, 2017, which claims priority to and benefit of Korean Patent Application No. 10-2016-0155013, filed on Nov. 21, 2016. The disclosures of the above-listed applications are hereby incorporated by reference herein in their entirety.

TECHNICAL FIELD

The present disclosure relates to an apparatus and a method for exercise type recognition that are capable of predicting the type of exercise being performed by a user based on the information of the orientation and movement of a user's particular body part acquired through sensors, and conveniently managing the user's exercise information through the prediction of the type of exercise.

BACKGROUND

With the development of information and communication technology, various portable electronic devices have flooded the market. In recent years, wearable computers having enhanced portability and convenience, e.g., electronic devices implemented as articles that can be worn on the body of a person such as glasses, watches and clothes, have attracted attention. One of the most widespread wearable computers is a smart watch that can be worn on a person's wrist. A smart watch can be easily worn and can perform various functions for the convenience of the user in spite of its small size, thereby contributing to the improvement of the quality of life of a user.

As a method of using a wearable computer such as a smart watch or the like, there is a method for managing exercise information such as the type, frequency and schedule of a user who exercises for fitness training or the like. Generally, activities related to exercise are performed in a public space such as a gymnasium or outdoors rather than personal space such as a home or office. Therefore, for the efficient and convenient management of exercise information, it is more desirable to use a wearable computer that is portable than to use a conventional computer such as a personal computer (PC) or the like.

A wearable computer having such an exercise management function has been already commercially available. For example, in a certain wearable computer, if a user manually inputs an exercise type before starting exercise, the wearable computer records information on the exercise on the assumption that the exercise being performed by the user has the exercise type inputted by the user. Such a conventional wearable computer cannot automatically recognize the type of exercise being performed by the user, and therefore, is constrained to rely on the input from the user for the exercise type recognition. Thus, whenever the type of exercise is converted, the user has to perform an input operation by operating the menu of the wearable computer. This reduces the efficiency and convenience of the wearable computer.

As another example, there is a technique of acquiring information related to physical activity of a user using sensors and estimating an exercise state of the user through the acquired information. However, this technique can merely carry out a rough prediction for the type and intensity of the exercise based on the user's moving speed, the body temperature, the heart rate and the like, and cannot accurately identify the type of the exercise including relatively precise motions, such as weight training or the like.

In addition, according to the related art, the types of exercise dealt with by the wearable computer are limited to the types previously stored in the wearable computer. Therefore, it is impossible to manage exercise newly methods acquired or created by the user.

SUMMARY

Embodiments of the present disclosure provide an exercise type recognition apparatus and an exercise type recognition method which are capable of automatically predicting the type of exercise being performed by a user without resort to user's manual input and conveniently managing the user exercise information through the prediction of the type of exercise.

In accordance with the present invention, there is provided an exercise type recognition apparatus comprising an exercise sensing wrist unit configured to acquire wrist exercise information including at least one of orientation information and motion information of a wrist of a user, an exercise sensing upper body unit configured to acquire upper body exercise information including at least one of orientation information and motion information of a torso of the user, and a control unit configured to calculate, using reference wrist exercise information and reference upper body exercise information corresponding to each of a plurality of exercise types, a first similarity degree between the reference wrist exercise information and the wrist exercise information and a second similarity degree between the reference upper body exercise information and the upper body exercise information, and determine an actual exercise type performed by the user among the plurality of exercise types based on the first similarity degree and the second similarity degree.

Further, the reference wrist exercise information includes reference wrist orientation information and reference wrist motion information, the reference upper body exercise information includes reference upper body orientation information and reference upper body motion information, and the control unit is configured to calculate the first similarity degree by respectively comparing the orientation information of the wrist and the motion information of the wrist with the reference wrist orientation information and the reference wrist motion information for each of the exercise types, and configured to calculate the second similarity degree by respectively comparing the orientation information of the upper body and the motion information of the upper body with the reference upper body orientation information and the reference upper body motion information for each of the exercise types.

Further, the control unit is configured to calculate a general similarity degree for each of the exercise types based on the first similarity degree and the second similarity degree and to provide the user with a result of sorting the exercise types according to a magnitude of the general similarity degree.

Further, the control unit is configured to output an exercise type having the general similarity degree equal to or greater than a predetermined value among the exercise types to the user as an actual exercise type candidate and to determine the actual exercise type from the actual exercise type candidate based on a selection of the user.

Further, the first reference similarity degree is larger than the second reference similarity degree, and the control unit is configured to provide the actual exercise type to the user from a corresponding part of a manual that stores information of each of the exercise types, together with guidance on a method of correction of the actual exercise type when the first similarity degree or the second similarity degree for the actual exercise type is less than a predetermined first reference similarity degree and equal to or greater than a predetermined second reference similarity degree, and to update the actual exercise type when the first similarity degree or the second similarity degree for the actual exercise type is less than the second reference similarity degree.

Further, the control unit is configured to output a predetermined warning notification to the user when the first similarity degree or the second similarity degree for the actual exercise type is less than the first reference similarity degree.

Further, the control unit is configured to, for an exercise routine in which one or more of the exercise types are combined in a predetermined order and for a predetermined number of repetitions, determine a previously performed part of the exercise routine based on a number of times the actual exercise type is consecutively performed, and guide a remaining part of the exercise routine, other than the previously performed part, to the user.

Further, the exercise types, the reference wrist exercise information and the reference upper body exercise information corresponding to each of the exercise types are updated based on an input from the user.

Further, the wrist exercise information includes at least one of velocity and acceleration of the wrist, and the upper body exercise information includes at least one of velocity and acceleration of the upper body.

Further, the apparatus comprises an exercise sensing foot unit configured to acquire foot exercise information including at least one of orientation information and motion information of a foot of the user, and the control unit is configured to further calculate a third similarity degree between a reference foot exercise information and the foot exercise information for each of the exercise types, and to determine the actual exercise type based on the third similarity degree.

Further, the apparatus comprises an exercise instrument information recognition unit installed on an exercise instrument used for an exercise performed by the user, and configured to acquire exercise instrument information on the exercise instrument, the control unit is configured to receive the exercise instrument information from the exercise instrument information recognition unit, and the exercise instrument information includes at least one of weight of the exercise instrument, velocity of the exercise instrument, acceleration of the exercise instrument and type of the exercise instrument.

Further, the control unit is configured to calculate an exercise repetition degree based on a degree at which at least one of the wrist exercise information and the upper body exercise information repeatedly appears within a predetermined range for a predetermined time, and to calculate the first similarity degree and the second similarity degree to determine the actual exercise type only when the exercise repetition degree is equal to or greater than a predetermined value.

Further, the storage unit is configured to store user physique information of the user, and the control unit is configured to calibrate the reference wrist exercise information and the reference upper body exercise information based on the user physique information, and to calculate the first similarity degree and the second similarity degree based on the calibrated reference wrist exercise information and the calibrated reference upper body exercise information.

In accordance with the present invention, there is provided an exercise type recognition method comprising a first step of acquiring wrist exercise information including at least one of orientation information and motion information of a wrist of a user, a second step of acquiring upper body exercise information including at least one of orientation information and motion information of a torso of the user, a third step of calculating, using reference wrist exercise information and reference upper body exercise information corresponding to each of a plurality of exercise types, a first similarity degree between the reference wrist exercise information and the wrist exercise information and a second similarity degree between the reference upper body exercise information and the upper body exercise information for each of the exercise types, and a fourth step of determining an actual exercise type performed by the user, among the exercise types, based on the first similarity degree and the second similarity degree.

Further, the reference wrist exercise information includes reference wrist orientation information and reference wrist motion information, the reference upper body exercise information includes reference upper body orientation information and reference upper body motion information, and the third step comprises a step of calculating, for each of the exercise types, the first similarity degree by respectively comparing the orientation information of the wrist and the motion information of the wrist with the reference wrist orientation information and the reference wrist motion information, and the second similarity degree by respectively comparing the orientation information of the upper body and the motion information of the upper body with the reference upper body orientation information and the reference upper body motion information.

Further, the third step comprises a step of calculating a general similarity degree for each of the exercise types based on the first similarity degree and the second similarity degree, and the fourth step comprises a step of providing the user with a result of sorting the exercise types according to a magnitude of the general similarity degree.

Further, the fourth step comprises a step of outputting an exercise type having the general similarity degree equal to or greater than a predetermined value among the exercise types to the user as an actual exercise type candidate, and determining the actual exercise type from the actual exercise type candidate based on a selection of the user.

Further, the first reference similarity degree is larger than the second reference similarity degree, and the fourth step comprises a step of providing the actual exercise type to the user from a corresponding part of a manual that stores information on each of the exercise types, together with guidance on a method of correction of the actual exercise type when the first similarity degree or the second similarity degree for the actual exercise type is less than a predetermined first reference similarity degree and equal to or greater than a predetermined second reference similarity degree, and updating the actual exercise type when the first similarity degree or the second similarity degree for the actual exercise type is less than the second reference similarity degree.

Further, the fourth step comprises a step of outputting a predetermined warning notification to the user when the first similarity degree or the second similarity degree for the actual exercise type is less than the first reference similarity degree.

Further, the fourth step comprises a step of determining, for an exercise routine in which one or more of the exercise types are combined in a predetermined order and for a predetermined number of repetitions, a previously performed part of the exercise routine based on a number of times the actual exercise type is consecutively performed, and guiding a remaining part of the exercise routine, other than the previously performed part, to the user.

Further, the exercise types, the reference wrist exercise information and the reference upper body exercise information corresponding to each of the exercise types are updated based on an input from the user.

Further, the wrist exercise information includes at least one of velocity and acceleration of the wrist, and the upper body exercise information includes at least one of velocity information and acceleration of the upper body.

Further, the method comprises a step of acquiring foot exercise information including at least one of orientation information and motion information of a foot of the user, the third step comprises a step of further calculating a third similarity degree between a reference foot exercise information and the foot exercise information for each of the exercise types, and the fourth step comprises a step of determining the actual exercise type based on the third similarity degree.

Further, the method comprises a step of receiving exercise instrument information on an exercise instrument, which is acquired by an exercise instrument information recognition unit installed on the exercise instrument used for an exercise performed by the user, and the exercise instrument information includes at least one of weight of the exercise instrument, velocity of the exercise instrument, acceleration of the exercise instrument and type of the exercise instrument.

Further, the fourth step comprises a step of calculating an exercise repetition degree based on a degree at which at least one of the wrist exercise information and the upper body exercise information repeatedly appears within a predetermined range for a predetermined time, and calculating the first similarity degree and the second similarity degree to determine the actual exercise type only when the exercise repetition degree is equal to or greater than a predetermined value.

Further, the third step comprises a step of calibrating the reference wrist exercise information and the reference upper body exercise information based on previously-stored user physique information of the user, and a step of calculating the first similarity degree and the second similarity degree based on the calibrated reference wrist exercise information and the calibrated reference upper body exercise information.

In accordance with the present invention, there is provided an exercise information management apparatus comprising an information acquiring unit mounted on an exercise instrument used for exercise performed by a user and configured to generate exercise instrument information including weight information of a portion of the exercise instrument which moves by a force exerted by the user, and an information processing unit configured to generate, based on the exercise instrument information, user exercise information including time-series information regarding a use of the exercise instrument by the user.

Further, the information processing unit is located in a portable electronic device of the user, and the information acquiring unit comprises a wireless communication module for transmitting the exercise instrument information to the information processing unit.

Further, the apparatus comprises an information storing unit which stores type information on a type of the exercise instrument on which the information acquiring unit is mounted, the information acquiring unit is configured to generate an exercise instrument recognition signal determined based on the type information and transmit the exercise instrument recognition signal to the information processing unit, and the information processing unit is configured to recognize, based on the exercise instrument recognition signal, the type of the exercise instrument used by the user.

Further, the information acquiring unit includes an acceleration sensor and is configured to determine whether said portion exists in the exercise instrument using an acceleration value measured by the acceleration sensor.

Further, the information processing unit is configured to recognize a type of the exercise instrument based on a result of a comparison of the exercise instrument information with predetermined reference exercise instrument information.

Further, the user exercise information includes at least one of type information of the exercise instrument, the weight information corresponding to each type of the exercise instrument, and information on a time period or number of times of the use of the exercise instrument by the user.

Further, the information acquiring unit comprises a pressure sensor which measures a pressure exerted thereon by said portion of the exercise instrument and is configured to generate the weight information based on a value of the pressure.

Further, the information acquiring unit further comprises an acceleration sensor which measures an acceleration of said portion of the exercise instrument and is configure to compensate the value of the pressure using a value of the acceleration so as to generate the weight information.

In accordance with the present invention, there is provided an exercise information management method comprising a first step of generating, using an information acquiring unit mounted on an exercise instrument used for exercise performed by a user, exercise instrument information including weight information of a portion of the exercise instrument which moves by a force exerted by the user, and a second step of generating, based on the exercise instrument information, user exercise information including time-series information regarding a use of the exercise instrument by the user.

Further, the second step is performed by a portable electronic device of the user, and the information acquiring unit comprises wireless communication module for transmitting the exercise instrument information to the portable electronic device.

Further, the first step comprises generating an exercise instrument recognition signal determined based on pre-stored type information on a type of the exercise instrument on which the information acquiring unit is mounted, and the second step comprises recognizing, based on the exercise instrument recognition signal, the type of the exercise instrument used by the user.

Further, the first step comprises determining whether said portion exists in the exercise instrument using an acceleration value measured by an acceleration sensor.

Further, the second step comprises recognizing a type of the exercise instrument based on a result of a comparison of the exercise instrument information with predetermined reference exercise instrument information.

Further, the user exercise information includes at least one of type information of the exercise instrument, the weight information corresponding to each type of the exercise instrument, and information on a time period or number of times of the use of the exercise instrument by the user.

Further, the information acquiring unit comprises a pressure sensor which measures a pressure exerted thereon by said portion of the exercise instrument, and the first step comprises generating the weight information based on a value of the pressure.

Further, the information acquiring unit further comprises an acceleration sensor which measures an acceleration of said portion of the exercise instrument, and the first step comprises compensating the value of the pressure using a value of the acceleration so as to generate the weight information.

According to an embodiment of the present disclosure, the information related to the orientation and movement of a user's wrist and upper body is acquired through sensors, and the acquired information is compared with the information stored in a storage unit. This makes it possible to predict the type of the exercise being performed by the user. Accordingly, the type of the exercise performed by the user can be accurately determined even with a small number of sensor devices. This makes it possible to enhance the convenience and efficiency. In addition, according to one embodiment of the present disclosure, it is possible to additionally provide an exercise correction function, a user-defined exercise type generation function and the like, which makes it possible to further enhance the convenience and efficiency.

BRIEF DESCRIPTION OF THE DRAWINGS

FIG. 3 is a view illustrating the flow of an exercise type recognition method carried out by the exercise type recognition apparatus according to an embodiment of the present disclosure.

FIGS. 4A to 4F are views for explaining a specific operation of the exercise type recognition apparatus according to an embodiment of the present disclosure.

FIG. 9 is a view illustrating the flow of an exercise information management method carried out by the exercise information management apparatus according to an embodiment of the present disclosure.

DETAILED DESCRIPTION

The advantages and features of exemplary embodiments of the present invention and methods of accomplishing them will be clearly understood from the following description of the embodiments taken in conjunction with the accompanying drawings. However, the present invention is not limited to those embodiments and may be implemented in various forms. It should be noted that the embodiments are provided to make a full disclosure and also to allow those skilled in the art to know the full scope of the present invention. Therefore, the present invention will be defined only by the scope of the appended claims.

In the following description, well-known functions and/or constitutions will not be described in detail if they would unnecessarily obscure the features of the present invention in unnecessary detail. Further, the terms to be described below are defined in consideration of their functions in the embodiments of the present invention and may vary depending on a user's or operator's intention or practice. Accordingly, the definition may be made on a basis of the content throughout the specification.

Hereinafter, the embodiments of the present invention will be described in detail with reference to the accompanying drawings.

Figure 1:
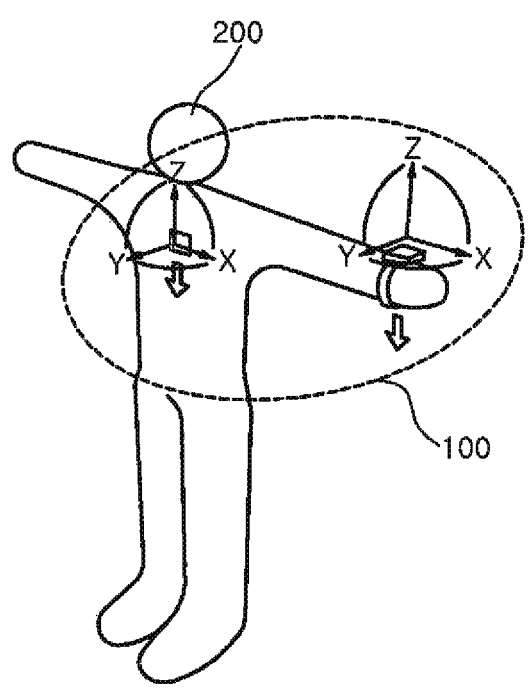
FIG. 1 is a view conceptually showing an exercise type recognition apparatus according to an embodiment of the present disclosure.

FIG. 1 is a view conceptually showing an exercise type recognition apparatus according to an embodiment of the present disclosure. As described at the beginning of this specification, a user 200 who performs exercise may manage his/her exercise information through an exercise type recognition apparatus 100 implemented in the form of a wearable computer for convenience and efficiency.

The exercise type recognition apparatus 100 according to an embodiment of the present disclosure may measure the exercise information of each of one or more specific body parts of the user 200. Although the body part for which the exercise information is to be measured may be any part, for the convenience of the user 200, it is necessary to obtain an accurate exercise type recognition result as far as possible by measuring a minimum number of body parts. Therefore, the exercise type recognition apparatus 100 according to an embodiment of the present disclosure is configured to accurately recognize the type of exercise of the user 200 based on only the exercise information on the wrist and the upper body (more specifically, the torso excluding the head and the arms) of the user 200.

In order to acquire the exercise information of the body part such as the wrist or the torso of the user 200, the exercise type recognition apparatus 100 may include a subcomponent mounted on the body of the user 200 as shown in FIG. 1 and configured to acquire exercise information. The exercise information acquired by such subcomponent may include orientation information and motion information. The orientation information may include information as to which direction the body part of the user information on which direction the body part of the user 200 faces in a three-dimensional coordinate system. The motion information may include information on the direction and velocity of the movement of the body part of the user 200 in the three-dimensional coordinate system, for example, velocity or acceleration when the wrist or the upper body of the user 200 moves in a specific direction.

Figure 2:
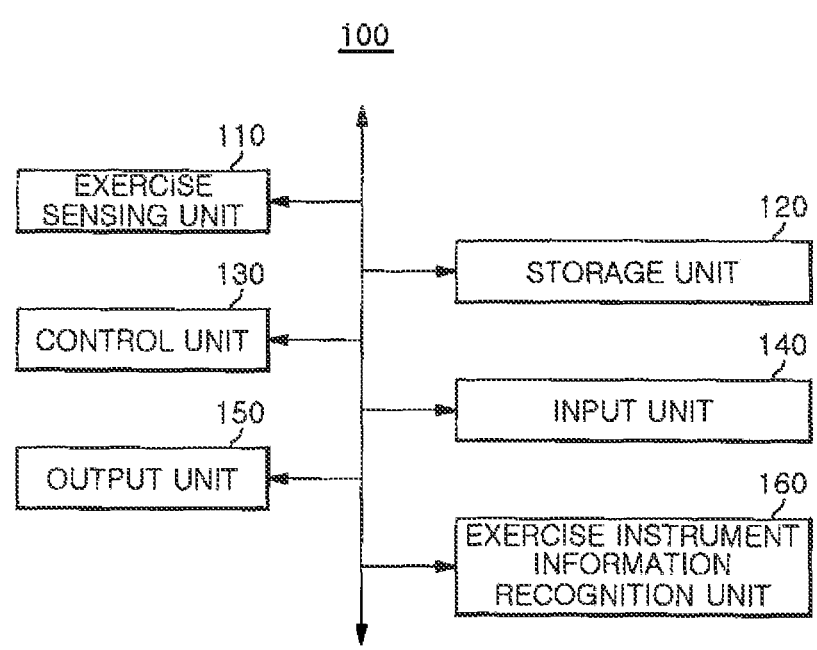
FIG. 2 is a view showing the configuration of the exercise type recognition apparatus according to an embodiment of the present disclosure.

FIG. 2 is a view showing the configuration of the exercise type recognition apparatus according to an embodiment of the present disclosure. The exercise type recognition apparatus 100 shown in FIG. 2 may include an exercise sensing unit 110, a storage unit 120, a control unit 130, an input unit 140, an output unit 150 and an exercise instrument information recognition unit 160. However, the exercise type recognition apparatus 100 shown in FIG. 2 is nothing more than one embodiment of the present disclosure. Therefore, the spirit of the present disclosure is not limited by the illustrating of FIG. 2.

The exercise sensing unit 110 may acquire exercise information such as orientation information and motion information of specific body parts of the user 200. According to an embodiment of the present disclosure, as described above, the wrist and the torso may be set as the specific body parts, but the present disclosure is not limited thereto. As a three-dimensional coordinate system for describing the orientation information and the motion information of the user 200, it may be possible to use widely-known coordinate systems such as a Cartesian coordinate system, a cylindrical coordinate system and a spherical coordinate system. However, the present disclosure is not necessarily limited thereto.

In order to achieve the object of the present disclosure described above, the exercise sensing unit 110 may include an exercise sensing wrist unit 111 for acquiring exercise information of the wrist of the user 200, and an exercise sensing upper body unit 112 for acquiring exercise information of the torso of the user 200. For the accurate measurement of exercise information, the exercise sensing wrist unit 111 may be mounted on the wrist of the user 200, and the exercise sensing upper body unit 112 may be mounted on the torso of the user 200. The exercise sensing wrist unit 111 may be mounted on only one wrist of the user 200 or may be mounted on both wrists of the user 200. The exercise sensing unit 110 may be implemented using one or more sensors such as a gravity sensor, a gyro sensor and an acceleration sensor. Such exercise information may be described in various ways. For example, the exercise information may be described on the basis of the ground direction detected through the gravity sensor (e.g., using the direction perpendicular to the ground as a z axis). Since the more detailed realization method of the exercise sensing unit 110 is obvious to a person skilled in the art, a detailed description thereof will be omitted here.

Optionally, the exercise sensing unit 110 may further include an additional component for collecting exercise information on another body part of the user 200 other than the wrist and torso. An example of such another body part is the foot. For example, the exercise sensing unit 110 may further include a foot exercise sensing unit (not shown) for acquiring foot exercise information such as orientation information and motion information of the foot of the user 200. By acquiring the foot movement information, it is possible to recognize the type of exercise for the exercise such as a leg press or the like, which moves only the lower body without special motion for the wrist and torso. By acquiring the exercise information on the wrist, torso and foot, it becomes possible to recognize almost all types of exercise.

Meanwhile, the main body of the exercise type recognition apparatus 100 according to an embodiment of the present disclosure is not limited in its implementation form. However, for the use convenience of the user 200, it is possible that the main body of the exercise type recognition apparatus 100 is implemented in the form of a wearable computer, particularly a smart watch which can be worn on the wrist of the user 200. As one example, the main body of the exercise type recognition apparatus 100 may be integrated with a commercially available general-purpose smart watch. In this case, a part of the smart watch may be used as a component of the exercise type recognition apparatus 100.

When the main body of the exercise type recognition apparatus 100 is implemented in such a form that the main body can be worn on the wrist of the user 200, the exercise sensing wrist unit 111 may be integrated with the main body of the exercise type recognition apparatus 100. However, the exercise sensing upper body unit 112 may be physically separated from the main body of the exercise type recognition apparatus 100. Components of the exercise sensing unit 110 separated from the main body may be realized by providing a communication module capable of communicating with the main body. Some components integrated with the main body among the components of the exercise sensing unit 110 may also communicate with the other components of the exercise sensing unit 110 separated from the main body, using a communication module included in itself or another component of the main body (for example, the control unit 130). The components such as the storage unit 120, the control unit 130, the input unit 140 and the output unit 150, which will be described below, are preferably implemented in the main body of the exercise type recognition apparatus 100.

The storage unit 120 may store a plurality of exercise types and may also store reference wrist exercise information and reference upper body exercise information corresponding to each of the exercise types. As used herein, the term "exercise type" may indicate a specific exercise motion such as a bench press, a squat, a deadlift, or the like. In addition, the exercise type may indicate a new type of exercise motion found or created by the user 200. Each of these exercise types may have reference wrist exercise information and reference upper body exercise information. For example, a squat may be defined as a type of exercise in which the wrist is moved up and down in a state of facing obliquely upward (hereinafter, the wrist facing upward is defined as the back of the wrist facing upward) and in which the torso is moved up and down in a upright posture. The reference wrist exercise information and the reference upper body exercise information corresponding to the squat may be determined based on this definition. In addition, when the exercise sensing unit 110 further acquires exercise information on another body part, the storage unit 120 may further store reference exercise information on said another body part.

Meanwhile, the exercise types and the reference wrist exercise information and the reference upper body exercise information corresponding to each of the exercise types, which are stored in the storage unit 120, may be updated based on the input from the user 200. In other words, the user 200 may store the new exercise type created by himself or obtained from another person in the storage unit 120, and may use the new exercise type as data for a new exercise. By this function, it is possible to infinitely expand the kinds of exercise that the user 200 can manage through the exercise type recognition apparatus 100 according to the embodiment of the present disclosure.

In addition to the reference exercise information, the storage unit 120 may further store data or an application program required by the exercise type recognition apparatus 100. For example, according to one embodiment of the present disclosure, the storage unit 120 may store a manual for providing a guide for each of the exercise types, the values of first and second reference similarities serving as the reference of the operation of the control unit 130, and the like. The storage unit 120 may be embodied as a computer-readable recording medium. Examples of the computer-readable recording medium include a magnetic medium such as a hard disk, a floppy disk or a magnetic tape, an optical medium such as a CD-ROM or a DVD, a magneto-optical medium such as a floptical disk or the like, and a hardware device specially configured to store and perform program instructions. Instead of directly including the storage unit 120, the exercise type recognition apparatus 100 may download information stored outside the exercise type recognition apparatus 100 via a network. This is obvious to those of ordinary skill in the art.

The control unit 130 may control other components of the exercise type recognition apparatus 100 so that the exercise type recognition apparatus 100 can perform a desired function. As a basic function, the control unit 130 may calculate the similarity for each of the exercise types by respectively comparing the reference wrist exercise information and the reference upper body exercise information corresponding to each of the exercise types stored in the storage unit 120 with the wrist exercise information and the upper body exercise information acquired by the exercise sensing unit 110. In some embodiments, based on the exercise information of the user 200 accumulated for a predetermined period of time by the exercise sensing unit 110, the control unit 130 may determine whether the user 200 is actually exercising or merely performing a daily life motion, through the degree of repetition of motion (for example, the repetition of motion in a similar direction and velocity over a certain number of times). Accordingly, the control unit 130 may be configured to calculate the degree of similarity only when the degree of repetition is equal to or greater than a certain level.

For example, the control unit 130 may cumulatively store wrist exercise information and upper body exercise information in the storage unit 120 during the predetermined period of time. Using the information accumulated in this manner, the control unit 130 may calculate the degree of repetition of exercise based on the degree of repetition of the wrist exercise information or the upper body exercise information appearing within a predetermined range during the predetermined period of time. The degree of repetition of exercise may be calculated for the wrist exercise information and the upper body exercise information, respectively. The control unit 130 may be configured to calculate the degree of similarity only when at least one (or both) of the degree of repetition of exercise on the wrist exercise information and the degree of repetition of exercise on the upper body exercise information is determined to be equal to or greater than a predetermined value.

Based on the result of the calculation, the control unit 130 may predict an exercise type corresponding to the exercise being performed by the user 200 among the exercise types stored in the storage unit 120. For example, the control unit 130 may predict the exercise type having the highest value of the calculated similarity as the exercise being performed by the user 200. In the meantime, due to differences in physique such as the height of a person or the like, there is a possibility that the movement distance or the movement radius of the wrist or the upper body may be different even when the person performs the same exercise. In order to calibrate the difference in physique, the control unit 130 may utilize the user physique information on the physique of the user 200 pre-stored in the storage unit 120, or the user physique information inputted from the user 200 through the input unit 140 to be described later. That is, based on the user physique information, the control unit 130 may calibrate the reference exercise information stored in the storage unit 120 in conformity with the physique information of the user 200 who is currently excising. The reference exercise information which has been corrected may be used for calculating the degree of similarity. In contrast, the control unit 130 may also estimate the physique condition of the user 200 through the exercise information acquired by the exercise sensing unit 110.

Other specific operations of the control unit 130 will be described later. The control unit 130 may be implemented using a computing device including a microprocessor. The control unit 130 may further include a communication module for communicating with components outside the exercise type recognition apparatus 100 or components separated from the main body of the exercise type recognition apparatus 100.

The input unit 140 may sense an input instruction inputted from the user 200 and may transmit the input instruction to the control unit 130. For example, the user 200 may operate the input unit 140 to select a specific exercise type from the exercise type prediction results outputted through the output unit 150 by the control unit 130. The input unit 140 may be implemented using an input device such as a classic keyboard or a mouse. Preferably, the input unit 140 may be implemented using a touch sensing panel integrally formed with a touch screen type display. A detailed implementation of the touch screen type display including the touch sensing panel is obvious to those skilled in the art, and therefore, a detailed description thereof will be omitted. In addition to the touch sensing panel, the exercise type recognition apparatus 100 according to an embodiment of the present disclosure may further include, as a part of the input unit 140, a button which can be operated through a physical operation such as pressing or touching, or a voice recognition device such as a microphone or the like.

The output unit 150 may output the specific information in the form recognizable by the user 200 under the control of the control unit 130. Such specific information may be, for example, an exercise type prediction result generated by the control unit 130. The output unit 150 may be realized to include a display device such as a liquid crystal display (LCD) or an organic light emitting diode (OLED), an audio output device such as a speaker or the like, or a vibration generator. More preferably, the output unit 150 may include a touch screen type display integrated with the touch sensing panel serving as the input unit 140 as described above. The exercise instrument information recognition unit 160 will be described later.

FIG. 3 is a view illustrating the flow of an exercise type recognition method carried out by the exercise type recognition apparatus according to an embodiment of the present disclosure. The respective steps of the exercise type recognition method according to an embodiment of the present disclosure will be described below with reference to FIG. 3. The description of parts overlapping with those of FIGS. 1 and 2 may be omitted. It should be noted that the following steps are not necessarily performed in order, and the order may be changed as necessary.

First, the wrist exercise information including the orientation information and the motion information of the wrist of the user 200 may be acquired using the exercise sensing wrist unit 111 of the exercise sensing unit 110 (S110). In addition, the upper body exercise information including the orientation information and the motion information of the torso of the user 200 may be acquired using the exercise sensing upper body unit 112 of the excise sensing unit 110 (S120).

Next, the control unit 130 may calculate the degree of similarity of each of the exercise types to the exercise performed by the user 200, using the exercise types pre-stored in the storage unit 120 and the reference wrist exercise information and the reference upper body exercise information corresponding to each of the exercise types (130). As described above, the reference wrist exercise information may include the reference wrist orientation information and the reference wrist motion information, and the reference upper body exercise information may include the reference upper body orientation information and the reference upper body motion information.

More specifically, the similarity degree calculation is performed as follows. For example, it is assumed that the above-mentioned bench press, squat and deadlift are stored in the storage unit 120 as exercise types. When the exercise sensing unit 110 acquires the exercise information of the user 200, the control unit 130 may first respectively compare the reference wrist orientation information and the reference wrist motion information stored in correspondence to the bench press with the wrist orientation information and the wrist motion information of the user 200, thereby calculating the degree of similarity (first degree of similarity) of the wrist exercise information on the bench press. In addition, the control unit 130 may respectively compare the reference upper body orientation information and the reference upper body motion information stored in correspondence to the bench press with the upper body orientation information and the upper body motion information of the user 200, thereby calculating the degree of similarity (second degree of similarity) of the upper body exercise information on the bench press. Such an operation may also be performed for the squat and the deadlift.

Further, as described above, the control unit 130 may calculate the degree of similarity to the reference exercise information including the reference orientation information and the reference motion information with respect to another body part of the user 200 other than the wrist and the upper body. For example, the control unit 130 may further calculate the degree of similarity (third degree of similarity) between the reference foot exercise information and the foot exercise information of the user 200. The calculated degree of similarity may be used as an additional data for the exercise type recognition.

After the above-described operation is performed, the control unit 130 may calculate the general similarity degree from two similarity degrees, i.e., the similarity degree of the wrist exercise information and the similarity degree of the upper body exercise information with respect to each of the exercise types. Such a general similarity degree may be obtained by taking a simple average of the two similarity degrees. However, it may also be possible to use other methods such as obtaining a weighted average by applying different weights to the two similarity degrees. In addition, when acquiring the exercise information on another body part such as the foot or the like other than the wrist and the torso, the above operation may be performed on another body part just like the wrist and the torso. Hereinafter, for the sake of convenience, it is assumed that only the exercise information of the wrist and the torso is acquired.

When the similarity degree calculation is completed, the control unit 130 may predict which type of exercise stored in the storage unit 120 corresponds to the exercise currently being performed by the user 200, and may determine the actual exercise type corresponding to the exercise actually performed by the user 200 (S140). For example, the control unit 130 may determine the exercise type having the largest general similarity degree as the actual exercise type corresponding to the exercise actually being performed by the user 200.

Further, the selection by the user 200 may be considered when determining the actual exercise type. For example, the control unit 130 may sort the respective exercise types stored in the storage unit 120 in the order of the general similarity degree. The result of this sorting may be provided to the user 200 via the output unit 150. There is no limit to the method of providing the sorting result. For example, the control unit 130 may sort all the exercise types stored in the storage unit 120 in order of the general similarity degree and may provide the same to the user 200. However, the control unit 130 may provide the user 200 with only the exercise types having the general similarity degree equal to or greater than a predetermined value in the order of the similarity degree. Alternatively, the control unit 130 may provide the user 200 with only a predetermined number of exercise types (for example, three exercise types having general similarity degrees larger than those of the others). The exercise types included in the list outputted to the user 200 in this way may be referred to as "actual exercise type candidates".

FIGS. 4A to 4F are views for explaining a specific operation of the exercise type recognition apparatus according to an embodiment of the present disclosure. That is, FIGS. 4A to 4F illustrate that the exercise type performed by the user 200 can be effectively predicted by acquiring the exercise information from the wrist and the torso.

Figure 4A:
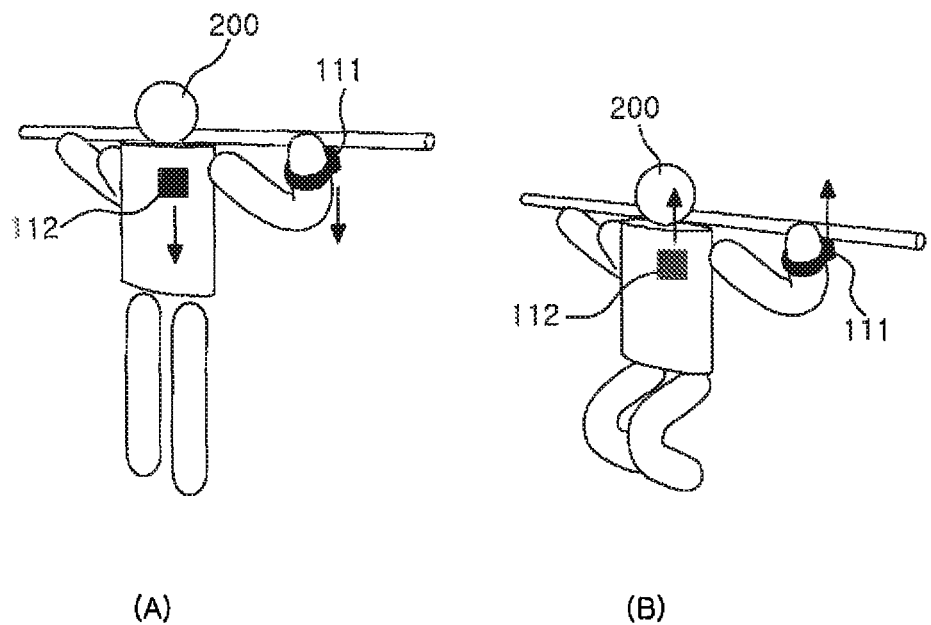

Referring to FIG. 4A, it can be seen that the wrist of the user 200 is moving up and down in a state in which the wrist is oriented obliquely upward with respect to the ground. It can also be noted that the torso of the user 200 is moving up and down in an upright posture with the same path and velocity as the wrist. This exercise may be defined as a squat.

Figure 4B:
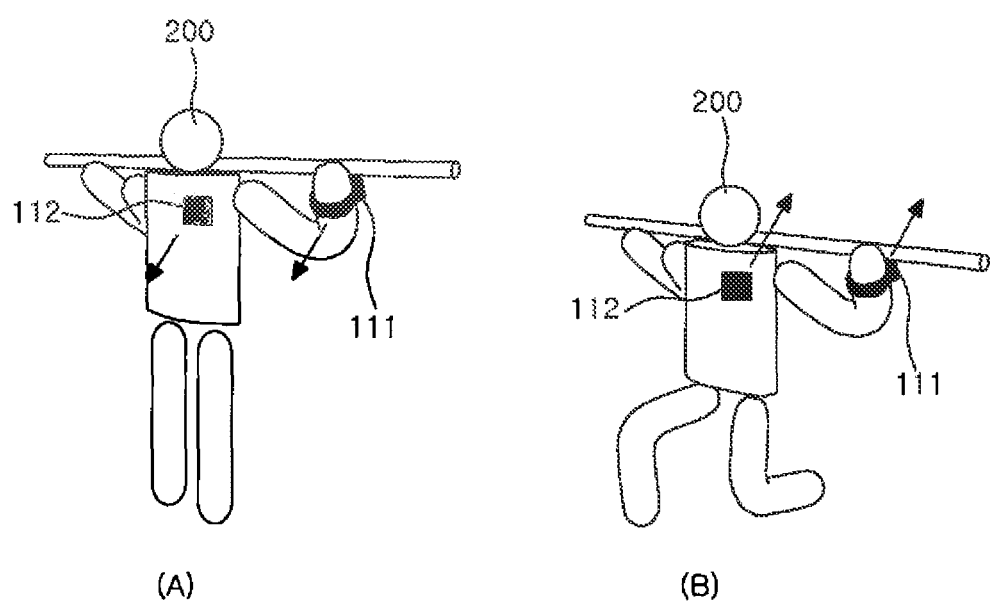

Referring to FIG. 4B, the wrist of the user 200 is oriented obliquely upward with respect to the ground as in the case of FIG. 4A. However, it can be noted that unlike FIG. 4A, the direction of the movement of the wrist of the user 200 is diagonal rather than vertical. In addition, the torso of the user 200 is also in an upright posture just like the case of FIG. 4A. However, unlike FIG. 4A, the direction of the movement of the torso of the user 200 is diagonal just like the wrist. This exercise may be defined as a lunge. That is, the squat and the lunge having the same orientation of the wrist and torso can be distinguished by the difference in movement.

Figure 4C:
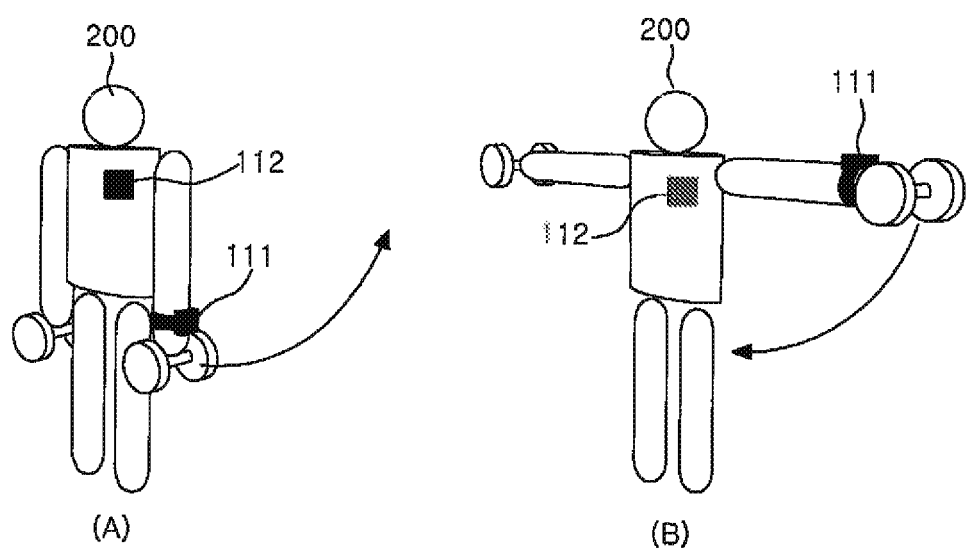

On the other hand, referring to FIG. 4C, it can be seen that the torso of the user 200 does not move while kept in an upright posture, and the wrist repeats the motion of drawing a quadrant about the shoulder as an axis. When the wrist reciprocates the quadrant once, the orientation of the wrist is gradually changed from the horizontal direction to the vertical direction and then from the vertical direction to the horizontal direction. This exercise may be defined as a side lateral raise.

Referring to FIG. 4D, the exercise shown in (A) and (B) of FIG. 4D and the exercise shown in (C) and (D) of FIG. 4D have the same exercise information of the wrist. However, it can be noted that (A) and (B) of FIG. 4D correspond to a backwardly lying posture in which the torso is rotated by an angle exceeding 90 degrees with respect to the upright posture, and (C) and (D) of FIG. 4D correspond to an obliquely lying posture in which the torso is rotated by an angle lower than 90 degrees with respect to the upright posture. A typical bench press is performed in a lying posture in which the torso is parallel to the ground. However, it can be seen through the torso's orientation information that the exercise shown in (A) and (B) of FIG. 4D and the exercise shown in (C) and (D) of FIG. 4D correspond to a decline bench press and an incline bench press, respectively, which are special types of a bench press.

Figure 4E:
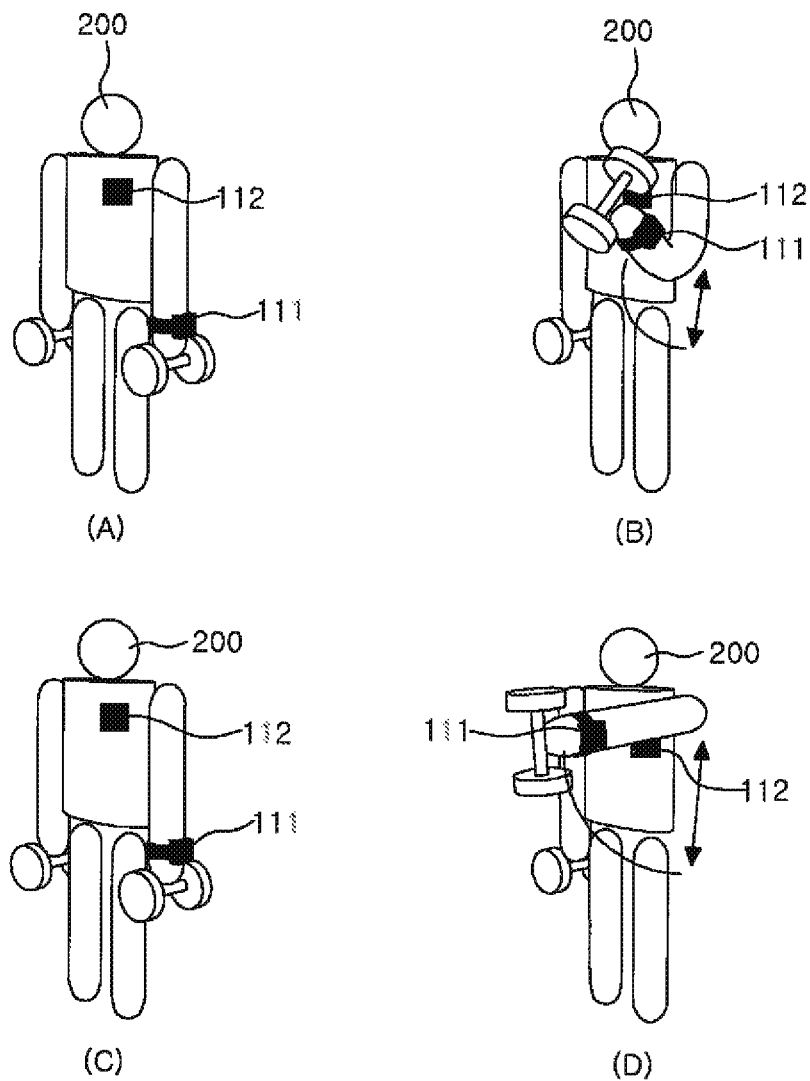

Next, referring to FIG. 4E, it can be seen that the exercise shown in (A) and (B) of FIG. 4E and the exercise shown in (C) and (D) of FIG. 4E have the same exercise information of the torso and have the same changing mode of the orientation of the wrist during the exercise, but the sizes of the trajectory drawn by the movement of the wrist are different from each other. That is, when storing the reference wrist motion information for the aforementioned exercise types in the storage unit 120, the radius of the trajectory of the wrist movement shown in (A) and (B) of FIG. 4E may be stored as the length of the elbow of an ordinary person, and the radius of the trajectory of the wrist movement shown in (C) and (D) of FIG. 4E may be stored as the total length of the arm of an ordinary person.

More specifically, information on the trajectory can be acquired as follows. First, the length of the trajectory can be calculated using the speed and elapsed time of the motion performed by the exercise sensing wrist unit 111. Additionally, the central angle of the trajectory can be calculated based on the change of the orientation of the exercise sensing wrist unit 111. Then, it is possible to determine the radius of the trajectory by acquiring a unique solution for the radius corresponding to the calculated length and central angle of the trajectory.

Finally, referring to FIG. 4F, it can be noted that the exercise shown in (A) and (B) of FIG. 4F and the exercise shown in (C) and (D) of FIG. 4F are identical in that the torso does not move while kept in an upright posture and are substantially similar in the trajectory drawn by the wrist in the course of the wrist movement and in the change of the orientation of the wrist. However, the typical motion principle may be used to distinguish between the two kinds of exercise. In the weight training, it is the principle that a body part such as the wrist moves quickly when moving in the force applying direction (i.e., the direction of a muscle contraction), but moves slowly when moving in the opposite direction (i.e., the direction of a muscle relaxation). In (A) and (B) of FIG. 4F, a force is applied when the wrist moves downward. Therefore, in this case, the reference wrist motion information may be defined as the wrist being quickly moved downward and slowly moved upward. Conversely, in (C) and (D) of FIG. 4F, a force is applied when the wrist moves upward. Therefore, in this case, the reference wrist motion information may be defined as the wrist being quickly moved upward and slowly moved downward. By referring to FIGS. 4D to 4F, it can be seen that according to an embodiment of the present disclosure, it is possible to recognize the subdivided exercise types through the orientation information and the motion information of the wrist and the torso.

Figure 5:
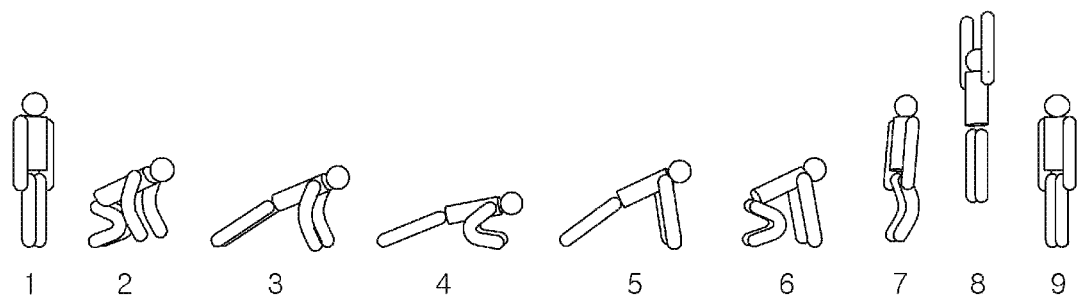
FIG. 5 is a view for explaining a function for recognizing patterned exercise among the functions of the exercise type recognition apparatus according to an embodiment of the present disclosure.

FIG. 5 is a view for explaining a function for recognizing patterned exercise among the functions of the exercise type recognition apparatus according to an embodiment of the present disclosure. FIG. 5 relates to a kind of grouping and shows that a plurality of exercise types can be stored in the storage unit 120 as one patterned exercise type. The exercise shown in FIG. 5 is called a burpee test and may be stored in the storage unit 120 as a patterned exercise type in which two types of exercise, i.e., push-up and jumping squat, are combined. That is, if it is determined that the user 200 has performed the jumping squat immediately after the push-up, the control unit 130 may recognize that the user 200 has performed the burpee test. Needless to say, the control unit 130 may provide both the burpee test and the jumping squat, as a result of the exercise type prediction, to the user 200 who has performed the jumping squat immediately after the push-up. Optionally, the control unit 130 may consider the patterned exercise type having a higher priority than a single exercise type with regard to the prediction of the exercise type recognition.

Referring again to FIG. 3, the control unit 130 may provide the user 200 with a list of actual exercise type candidates as described above. The user 200 may select, through the input unit 140, the type of exercise actually being performed by the user among the actual exercise type candidates. This selection corresponds to the determination of the actual type of exercise that the user 200 is currently performing. As described above, such determination may be performed by the control unit 130 based on the similarity degree without resort to the input of the user 200.

In the above example, when the control unit 130 presents a decline bench press, an ordinary bench press and an incline bench press as actual exercise type candidates in the order of the general similarity degree, the user 200 may select the decline bench press, thereby confirming that the control unit 130 has performed a correct recognition. Alternatively, the user 200, who is actually performing the ordinary bench press, may determine the type of exercise being performed by himself or herself as an ordinary bench press by selecting the ordinary bench press having a lower general similarity degree. In this case, it may be interpreted that the user 200 is exercising in a state in which the body is too inclined to be regarded as an ordinary bench press. Therefore, the control unit 130 may provide the user 200 with a manual of the ordinary bench press stored in the storage unit 120 as an exercise correction function that induces the user to perform an ordinary bench press with a correct posture. Further, the control unit 130 may recommend the user 200 to newly select the decline bench press which is a type of exercise having a highest similarity degree determined by the control unit 130 as the actual exercise type instead of the ordinary bench press.

More specifically, for example, the control unit 130 may perform the above-described exercise correction function when the similarity degree of the wrist exercise information or the similarity degree of the upper body exercise information with respect to the exercise type determined as the exercise being performed by the user 200 is smaller than a predetermined first reference similarity degree and larger than a predetermined second reference similarity degree (where the first reference similarity degree is preferably larger than the second reference similarity degree). At this time, in addition to performing the exercise correction function, the control unit 130 may output a predetermined notification through the output unit 150 so that the user 200 can immediately recognize that the exercise of the user 200 is incorrect. The predetermined notification may be a visual notification such as a warning text or the like, an audible notification such as a beep sound or the like, or tactile notification such as a vibration or the like. As the similarity degree determination reference, it may be possible to use the similarity degree of the wrist exercise information or the similarity degree of the upper body exercise information as described above. The general similarity degree may also be used.

Figure 6:
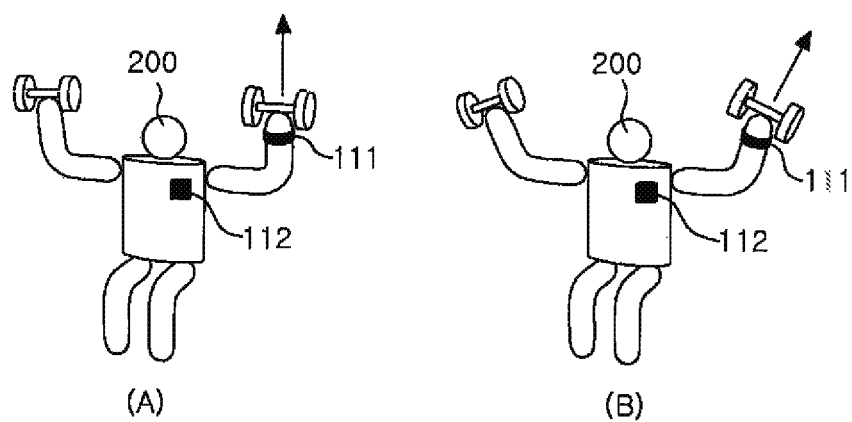
FIG. 6 is a view for explaining an exercise correction function among the functions of the exercise type recognition apparatus according to an embodiment of the present disclosure.

FIG. 6 is a view for explaining an exercise correction function among the functions of the exercise type recognition apparatus according to an embodiment of the present disclosure. FIG. 6(A) shows a method of lifting a dumbbell correctly. It can be seen that the wrist with a dumbbell has to be moved in a vertical direction. On the other hand, FIG. 6(B) shows an incorrect posture in which the wrist with a dumbbell is moved obliquely upward. When the user 200 takes an incorrect posture shown in FIG. 6(B), the control unit 130 may guide the user 200 to take a correct posture through the exercise correction function based on the similarity degree which has been calculated to be a low level.

However, it is necessary to determine whether the user 200 is performing exercise in the wrong way or intentionally switching the exercise to another exercise. In a method of making such determination, if the similarity degree to the determined exercise type is very low and falls below the second reference similarity degree, the control unit 130 may determine that the exercise is not wrong but the exercise is switched.

In fact, it is common that when the user switches the kind of exercise, there is a slight resting period between one exercise and another exercise (for example, a time to take a break or move to another exercise instrument). It is highly likely that the motion shown by the user in the resting period is not similar to any exercise type. If the user 200 shows a motion having an extremely low similarity degree (less than the second reference similarity degree as illustrated above) to the determined exercise type, the control unit 130 may determine that the user is in a resting period, and may suspend the prediction operation until the exercise type whose similarity degree is equal to or higher than the second reference similarity degree is detected. If the exercise type whose similarity degree is equal to or higher than the second reference similarity degree is detected, the control unit 130 may perform a new prediction and determination operation.

For more accurate operation, the control unit 130 may determine that the user 200 is in a resting period when the period of time in which the similarity degree falls below the second reference similarity degree is maintained for a predetermined time or more. Alternatively, the user 200 may inform the control unit 130 that the user 200 wants to switch the exercise, by using an input through the input unit 140, for example, an operation of pressing a specific button.

On the other hand, the control unit 130 may update the actual exercise type based on the new similarity degree value every time the similarity degree is newly calculated. However, even if the similarity degree is newly calculated, the actual exercise type may not be updated unless a predetermined time is not elapsed from the time when the actual exercise type is finally updated. In this case, the control unit 130 may induce the user to take a correct posture according to the actual exercise type, instead of updating the actual exercise type. Furthermore, the control unit 130 may update the actual exercise type to be another exercise type having a highest similarity degree only when the newly calculated similarity degree to the actual exercise type falls below the second reference similarity degree. This makes it possible to prevent the actual exercise type from being excessively frequently switched.

According to the embodiment, if a state in which the motion is so inconsistent (for example, a state in which the similarity degree falls below the second reference similarity degree and then returns to above the first Reference similarity degree, or a state in which the similarity degree changing in a predetermined change amount or more appears a predetermined number of times or more) is detected, the control unit 130 may determine that the exercise is incorrectly performed, and may execute an exercise correction function.

Meanwhile, although it is determined that the exercise performed by the user 200 is switched to another exercise as the similarity degree falls below the second reference similarity degree, said another exercise may not be similar to any of the exercise types stored in the storage unit 120. In this case, the user 200 may directly store said another exercise as a new exercise type in the storage unit 120 through the input unit 140.

The control unit 130 may score the exercise goal achievement rate of the user 200 based on how high similarity degree the user 200 has performed the exercise or whether the user 200 has correctly followed the plurality of exercise types in the predetermined order, and may provide the exercise goal achievement rate to the user 200. The user 200 may know through the exercise goal achievement rate how faithfully the user 200 is performing the exercise.

Based on the functions as described above, the exercise type recognition apparatus 100 according to an embodiment of the present invention may perform an exercise management function for the user 200. Specifically, the control unit 130 may record, in the storage unit 120, information such as the type, order and frequency of the exercise performed by the user 200 at a specific date and time. In addition, the control unit 130 may record, in the storage unit 120, how correctly the exercise of the user 200 has been performed, based on the information such as the similarity degree or the like. Moreover, the user 200 may pre-store, in the storage unit 120, an exercise plan according to the date and time (e.g., twelve squats after 15 push-ups). In this case, the control unit 130 may present the exercise plan to the user 200 at the date and time. During the exercise performed by the user 200, the control unit 130 may inform the user 200 of the exercise type to be performed next according to the exercise plan and the number of execution times of the exercise (for example, the control unit 130 may inform the user 200 who has already performed 13 push-ups that 2 push-ups and 12 squats remain).

On the other hand, the guidance according to this exercise routine may be performed based on the prediction and determination of the control unit 130, regardless of the specific date and time. For example, when the exercise type determined as the exercise performed by the user 200 belongs to a specific exercise routine, or when the user 200 is exercising after selecting a specific exercise routine, the control unit 130 determines whether the exercise type currently performed by the user 200 has been consecutively performed a predetermined number of times defined in the exercise routine. If it is determined that the exercise type has been consecutively performed as defined in the exercise routine, the control unit 130 may guide the next exercise type in the exercise routine to the user 200. That is, the control unit 130 may determine which part of the exercise routine has been previously performed, and may guide the remaining part of the exercise routine to the user 200. In this way, by comparing the exercise performed by the user 200 with the stored exercise routine, it is possible to effectively predict the exercise type which the user 200 will perform, even if there are two or more types of exercise that are hard to distinguish due to the similar movement of the wrist and/or the torso. Thus, the functions of the present disclosure can be supplemented. In addition, the exercise type recognition apparatus 100 according to an embodiment of the present disclosure can perform all the general functions of an exercise scheduler currently in widespread use.

As described above, according to an embodiment of the present disclosure, it is possible to accurately discriminate the type of exercise performed by the user 200 using only a small number of sensor devices. In addition, according to an embodiment of the present disclosure, it is possible to additionally provide an exercise correction function, a user-defined exercise type generation function and the like to the user 200. This makes it possible to further enhance the convenience and the efficiency.

Meanwhile, the exercise type recognition apparatus 100 according to an embodiment of the present disclosure may perform a function of recognizing exercise instrument information through communication with an exercise instrument or mechanism, in addition to the exercise type recognition and management function described above. These additional functions will be described below.

Figure 7A:
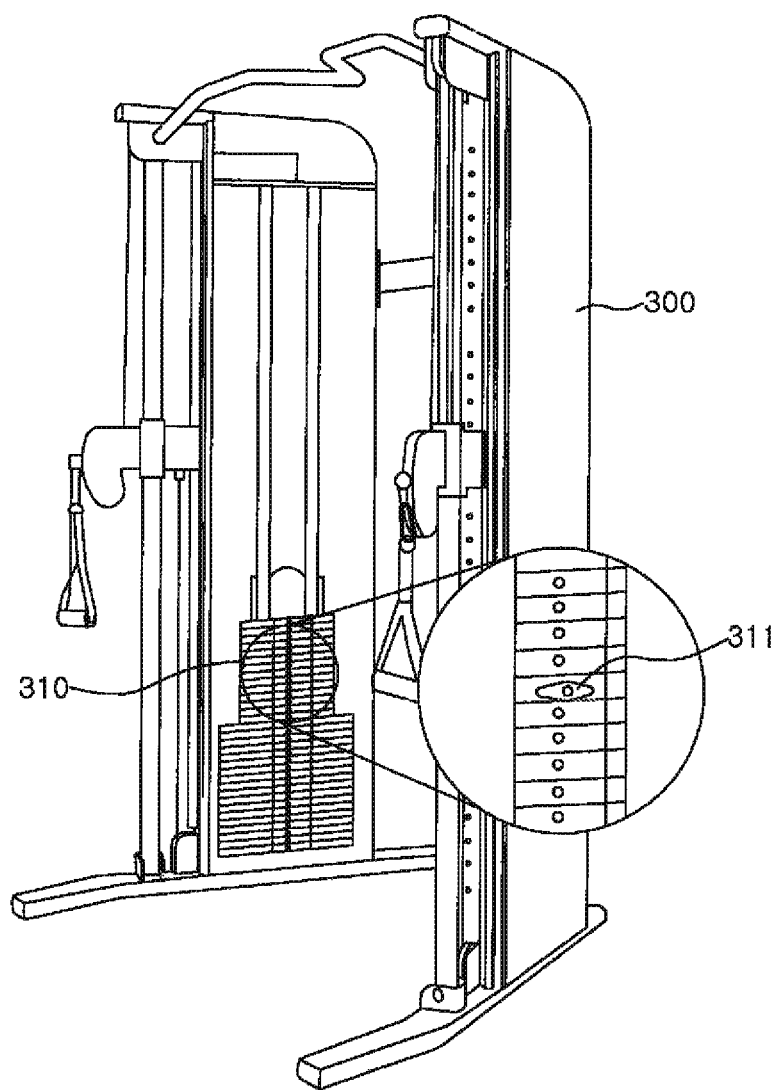
FIGS. 7A to 7C are views for explaining an exercise instrument information recognition function according to an embodiment of the present disclosure.
Figure 7B:
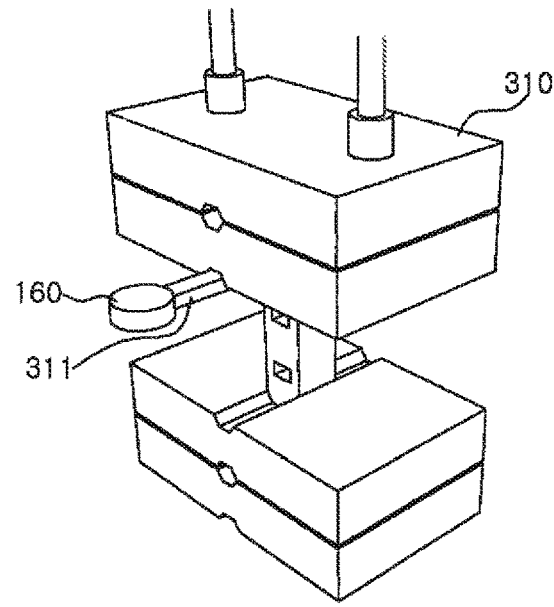
Figure 7C:
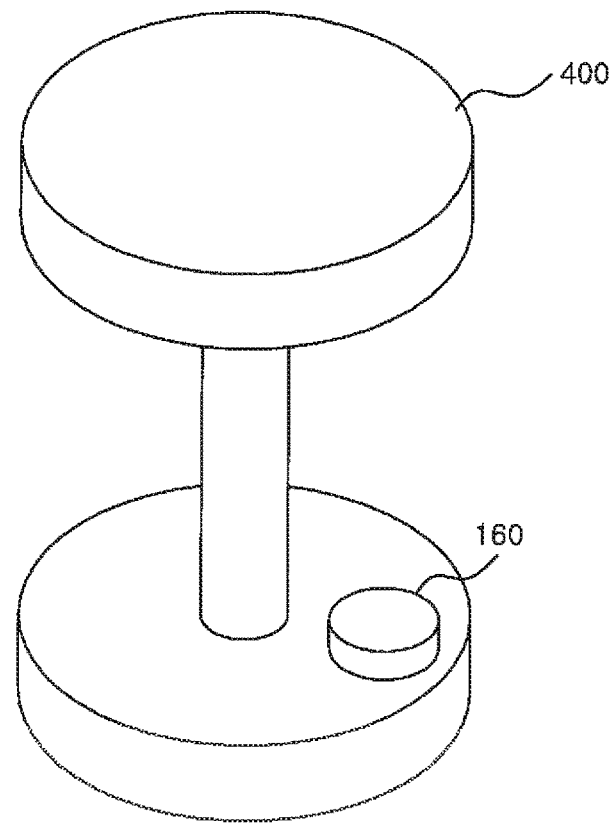

FIGS. 7A to 7C are views for explaining an exercise instrument information recognition function according to an embodiment of the present disclosure. Generally, a plurality of disks having a predetermined unit weight exists in an exercise instrument for weight training. For example, assuming that there is a weight training machine 300 in which the weight thereof is adjustable using a plurality of 5 kg disks as shown in FIG. 7A, the user 200 of the machine 300 may insert a fixing pin 311 into the sixth disk from the top among the plurality of disks 310 of the machine 300 when the user 200 wishes to set the weight of the weight training machine 300 as 30 kg. Then, the sixth disk into which the fixing pin 311 is inserted and the first to fifth disks above the sixth disk, i.e., a total of six disks having a weight of 30 kg, can be used for the exercise of the user 200.

In this case, an exercise instrument information recognition device including a pressure sensor and an acceleration sensor may be mounted on a component of an exercise instrument such as the fixing pin 311 or the like as shown in FIG. 7B. The exercise instrument information recognition device may be an exercise instrument information recognition unit 160 as a component of the exercise type recognition apparatus 100. The exercise instrument information recognition unit 160 may be implemented in proximity to the exercise instrument used by the user 200 while being physically separated from the main body of the exercise type recognition apparatus 100. The exercise instrument information recognition unit 160 may include a communication module for communicating with the main body of the exercise type recognition apparatus 100. The control unit 130 may receive the information acquired by the exercise instrument information recognition unit 160 through wireless communication.

The exercise type recognition apparatus 100 may automatically know the weight with which the user 200 has performed the exercise, based on the weight information acquired by the pressure sensor in the exercise instrument information recognition unit 160. A description will be made more specifically using the illustration of the disks 310 and the fixing pin 311. As the number of the disks 310 used by the user 200 for exercise increases, the load applied to the fixing pin 311 increases in proportion thereto. Such a load may be sensed by the pressure sensor in the exercise instrument information recognition unit 160 mounted on the fixing pin 311.

However, the weight information acquired by the pressure sensor may be inaccurate due to the inertial force when the disks 310 undergo acceleration movement. Therefore, the acceleration information including the information on the magnitude and direction acquired by the acceleration sensor in the exercise instrument information recognition unit 160 may be used for correcting the weight information. In addition, the exercise instrument information recognition unit 160 may also include a storage module for storing information on the type of the exercise instrument on which the exercise instrument information recognition unit 160 is installed. The information on the type of the exercise instrument may also be transmitted to the control unit 130 through wireless communication. Then, the control unit 130 may automatically acquire information on the weight with which the user 200 has performed the exercise, and may execute the exercise management function for the user 200 based on the acquired information.

Alternatively, as for a relatively simple exercise instrument such as a dumbbell or the like which does not have a weight adjustment function using disks or plates, as shown in FIG. 7C, a small device provided with at least one of a pressure sensor and an acceleration sensor and having a communication function may be attached to an exercise instrument 400 as an exercise instrument information recognition unit 160. Then, the device corresponding to the exercise instrument information recognition unit 160 may realize through the sensor that the user 200 is performing exercise with the exercise instrument 400, and may transmit the exercise instrument information including the information on the kind and weight of the exercise instrument 400 to the control unit 130.

The exercise instrument information acquired from the exercise instrument information recognition unit 160 in this manner may supplement the information acquired by other components of the exercise type recognition apparatus 100. For example, when the control unit 130 realizes that the user is performing bench press, the control unit 130 may receive information on the kind and weight of the exercise instrument such as a barbell or the like used for bench press by the user 200, the velocity and acceleration during exercise, and the like from the exercise instrument information recognition unit 160. The velocity information and the acceleration information may include magnitude information and direction information, respectively. The control unit 130 may store, in the storage unit 120, the information related to the exercise of the user 200 acquired by the exercise sensing unit 110 and the exercise instrument information recognition unit 160 in this manner.

The above-described function of communicating with the exercise instrument or mechanism may be easily realized by adding only the sensor and the communication module to the exercise instrument or machine provided in a health club or the like. The information acquired by this function may be shared by the user 200 of the exercise type recognition apparatus 100 and the health club through wireless communication. In this case, the health club may easily manage the exercise information of members by managing the system including the exercise instrument or machine having a communication function and the exercise type recognition apparatus 100 possessed by each of the members of the health club through a network.

More specifically, the information acquired by the exercise sensing unit 110 and the exercise instrument information recognition unit 160 may be converted into an integrated data as a daily/hourly exercise record of the user by the exercise type recognition apparatus 100. The integrated data stored in the storage unit 120 of the exercise type recognition apparatus 100 may be transmitted to a specific device (e.g., a server, a computer, a smart phone, or the like) through various communication methods such as long term evolution (LTE), Wi-Fi and the like. In addition, the exercise type recognition apparatus 100 of the user may receive data such as a next exercise plan or an exercise posture from the specific device.

Hereinafter, the embodiment introduced above with reference to FIGS. 7A to 7C will be described in detail with reference to FIGS. 8A to 9.

Figure 8A:
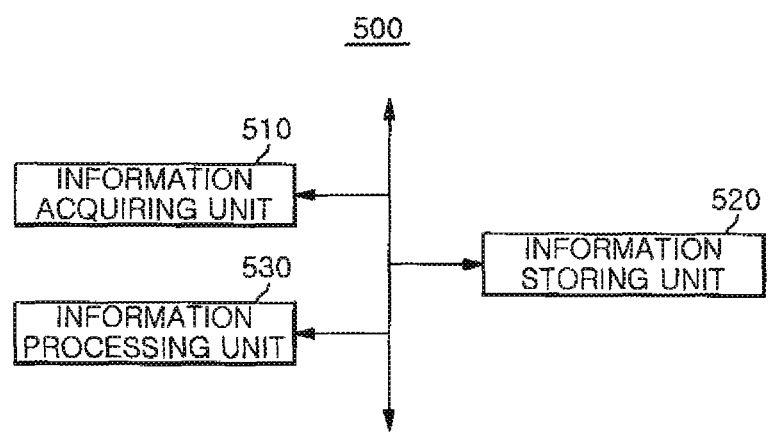
FIGS. 8A to 8C are views for explaining showing the configuration of an exercise information management apparatus according to an embodiment of the present disclosure.
Figure 8B:
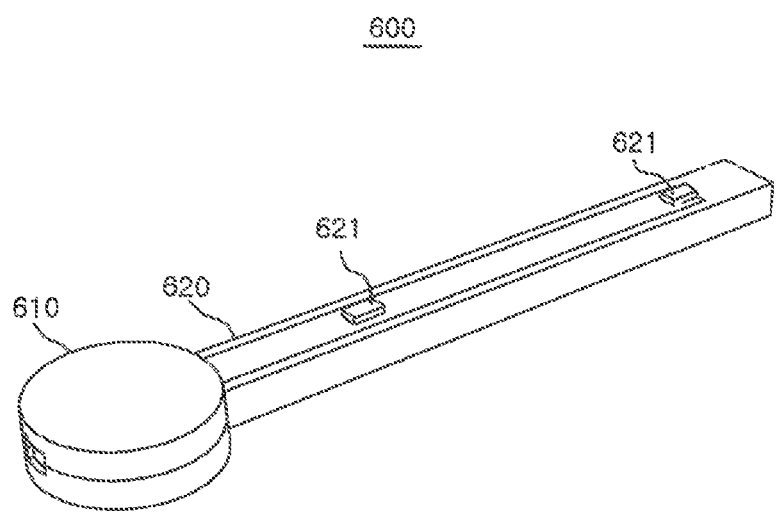
Figure 8C:
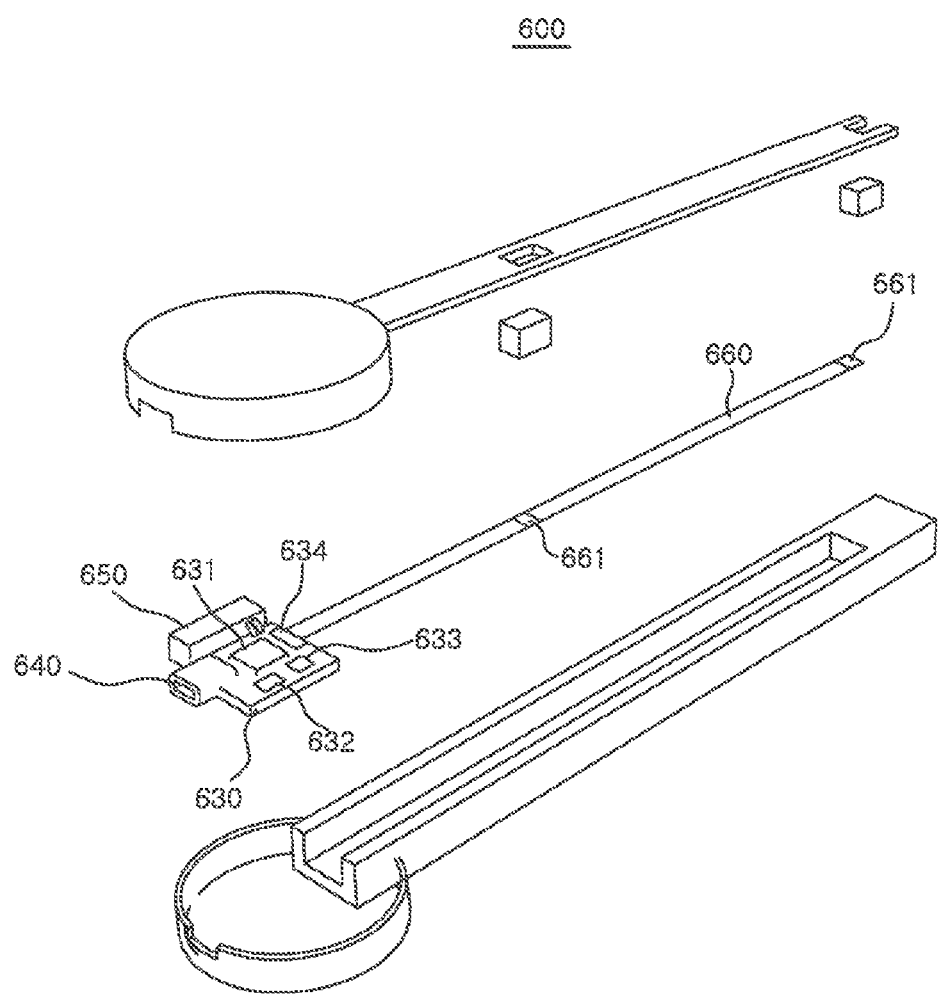

FIGS. 8A to 8C are views for explaining showing the configuration of an exercise information management apparatus according to an embodiment of the present disclosure. The exercise information management apparatus 500 shown in FIG. 8A may comprise an information acquiring unit 510, an information storing unit 520 and an information processing unit 530. However, the exercise information management apparatus 500 shown in FIG. 8A is nothing more than one embodiment of the present disclosure. Therefore, the spirit of the present disclosure is not limited by the illustrating of FIG. 8A.

The information acquiring unit 510 may be mounted on an exercise instrument used for exercise performed by a user 200 and configured to generate exercise instrument information including weight information of a portion of the exercise instrument which moves by a force exerted by the user 200. For example, it may be assumed that the exercise instrument is the weight training machine 300 illustrated in FIG. 7A, said portion can be the disks 310. In this assumption, if six disks among the disks 310 move by the exercise performed by the user 200, the weight of said portion will be 30 kg. However, if the user 200 stops performing the exercise such that none of the disks 310 moves, it may be considered that said portion does not exist anymore, and thus, the weight of said portion will be 0. The determination on whether the portion exists in the exercise instrument can be carried out by an acceleration sensor to be described later.

The information storing unit 520 may store type information on a type of the exercise instrument on which the information acquiring unit 510 is mounted. The information storing unit 520 may be also mounted on the exercise instrument on which the information acquiring unit 510 is mounted. For example, if the information acquiring unit 510 is mounted on a barbell used for bench press, the information storing unit 520 can be also mounted on said barbell with the information acquiring unit 510. In this case, the information storing unit 520 may store type information indicating that the type of the exercise instrument on which the information acquiring unit 510 is mounted is a barbell. Then, based on the type information stored in the information storing unit 520, the information acquiring unit 510 can recognize that the information acquiring unit 510 is currently mounted on a barbell. If the information acquiring unit 510 and the information storing unit 520 have been moved from the barbell to a dumbbell which is a new exercise instrument, the type information stored in the information storing unit 520 may be modified so as to indicate the dumbbell instead of the barbell.

The information acquiring unit 510 may generate an exercise instrument recognition signal based on the type information and transmit the exercise instrument recognition signal to the information processing unit 530 to be described later. The information processing unit 530 may recognize, by receiving the exercise instrument recognition signal and extracting information included in the received signal, the type of the exercise instrument on which the information acquiring unit 510 is mounted. In some embodiments, the information processing unit 530 may be, spatially separated from the information acquiring unit 510 and information storing unit 520, located on a portable electronic device of the user 200. For example, the information processing unit 530 may be implemented using a microprocessor such as central processing unit (CPU) of the portable electronic device. In this case, the information acquiring unit 510 may comprise a wireless communication module for transmitting the exercise instrument information or the exercise instrument recognition signal to the information processing unit 530.

The information processing unit 530, based on the exercise instrument information, may generate user exercise information including time-series information regarding a use of the exercise instrument by the user. For example, the user exercise information may include type information of the exercise instrument, the weight information corresponding to each type of the exercise instrument, and information on a time period or number of times of the use of the exercise instrument by the user 200. Thus, from the user exercise information, the user 200 can easily grasp his or her exercise history (for example, on Jan. 1, 2018, the user 200 performed exercise using a 50 kg barbell twenty times in a time period from 13:00 to 13:02 and exercise using a 10 kg dumbbell thirty times in a time period from 13:30 to 13:33).

In order to implement of the aforementioned function, each of a plurality of exercise instruments used by a user 200 may have its own information acquiring unit 510 and information storing unit 520. The information processing unit 530 may recognize, based on the weight information included in the exercise instrument information transmitted from the information acquiring unit 510 belonging to each of the exercise instruments, the type of the exercise instrument currently used by the user 200. More specifically, based on the weight information, the information processing unit 530 can recognize a specific exercise instrument which generated the weight information indicating a weight higher than 0 (in other words, an exercise instrument having the portion which moves by a force exerted by the user 200), thereby determining that the specific exercise instrument is currently used by the user 200 for performing exercise. In some embodiments, the information processing unit 530 can recognize an exercise instrument which generated the weight information indicating a weight higher than predetermined value (for example, 5 kg) so as to determine which exercise instrument is currently used by the user 200.

In some embodiments, the information processing unit 530 may recognize the type of the exercise instrument used by user 200 based on a result of a comparison of the exercise instrument information with predetermined reference exercise instrument information. The reference exercise instrument information may include a relationship between the weight information and the type of the exercise instrument. The information processing unit 530 may determine, based on the relationship, that a 5 kg dumbbell is currently used by the user 200 when the weight indicated by the weight information included in the exercise instrument information is 5 kg, or may determine that a 50 kg barbell is currently used by the user 200 when the weight is 50 kg. Such determination is based on a common knowledge that a barbell is generally heavier than a dumbbell. The reference exercise instrument information may be freely revised by the user 200.

FIGS. 8B and 8C are views for describing an embodiment in which the exercise information management apparatus 500 illustrated in FIG. 8A is implemented as a form of a fixing pin 600 for fixing the disks 310 illustrated in FIGS. 7A and 7B. The fixing pin 600 illustrated in FIGS. 8B and 8C may be substantially identical to the fixing pin 311 explained referring FIG. 7B.

As illustrated in FIG. 8B, the fixing pin 600 may include a main body 610 which has a cylindrical shape and functions as a handle and a supporting bar 620 which is attached to and extends from the main body 610. On the supporting bar 620, one or more press transfer units 621 may be mounted. The press transfer units 621 may transfer the load of the portion of the exercise instrument which moves by a force exerted by the user 200 (for example, the disks 310) to one or more pressure sensors 661 to be described later.

As illustrated in FIG. 8C, the fixing pin 600 further includes a variety of components disposed in the internal space formed by the main body 610 and the supporting bar 620. As examples of the components, a mainboard 630, a transmission port 640 and a battery 650 may be disposed in the internal surface formed by the main body 610, and an internal bar 660 and pressure sensors 661 may be disposed in the internal surface formed by the supporting bar 620. The mainboard 630 may include a processor 631, a communication module 632, an acceleration sensor 633 and a storage device 634.

The pressure sensors 661 mounted on the internal bar 660 may measure a pressure exerted thereon by said portion of the exercise instrument. Further, the acceleration sensor 633 may measure the acceleration of the fixing pin 600. Since the fixing pin 600 moves identically with said portion of the exercise instrument such as disks 310, the acceleration measured by the acceleration sensor 633 can be considered as the acceleration of said portion.

The processor 631 may generate the weight information based on a value of the pressure measured by the pressure sensors 661. However, as explained above, the weight information generated only based on the pressure sensors 661 may be incorrect if said portion performs an accelerated motion. Generally, an object whose weight is to be measured should be placed on a scale without movement in order to obtain a correct weight value. In contrast, in embodiments of the present disclosure, the weight of the disks 310 may be measured even when the disks 310 move. Accordingly, the processor 631 can compensate the value of the pressure measured by the pressure sensors 661 using the value of the acceleration measured by the acceleration sensor 633 so as to generate the weight information. By such compensation process, the weight information can be more correctly acquired.

The main board 630 may receive electric power from the battery 650 or the outside of the fixing pin 600 via the transmission port 640. The storage device 634 may store information required by the processor 631 (for example, information on a type of the exercise instrument). Further, the exercise instrument information including the weight information, the exercise instrument recognition signal or the like can be transmitted to the outside of the fixing pin 600 via the communication module 632 or the transmission port 640.

Among each component included in the fixing pin 600 as described with reference to FIGS. 8B and 8C, the storage device 634 can correspond to the information storing unit 520 of the exercise information management apparatus 500 illustrated in FIG. 8A, and components other than the storage device 634 can correspond to the information acquiring unit 510 of the exercise information management apparatus 500. The information processing unit 530 may be implemented by the processor 631, or by an external device such as a portable electronic device of the user 200 which is separated from the fixing pin 600 as explained above.

FIG. 9 is a view illustrating the flow of an exercise information management method carried out by the exercise information management apparatus according to an embodiment of the present disclosure. The respective steps of the exercise information management method according to an embodiment of the present disclosure will be described below with reference to FIG. 9. The description of parts overlapping with those of FIGS. 8A to 8C may be omitted.

It should be noted that the following steps are not necessarily performed in order, and the order may be changed as necessary.

First, the information acquiring unit 510 may be mounted on an exercise instrument used for exercise performed by the user 200 (S210). In addition, using the information acquiring unit 510, the exercise instrument information including the weight information of a portion of the exercise instrument which moves by a force exerted by the user 200 may be generated (S220). Next, using the information processing unit 530, the user exercise information including the time-series information regarding a use of the exercise instrument by the user 200 may be generated based on the exercise instrument information (S230).

According to the embodiment of the present disclosure explained with reference to FIGS. 8A to 9, it becomes possible to obtain various kinds of information on exercise which has been performed by the user 200. Therefore, the historical exercise information of the user 200 can be effectively managed.

The combinations of respective sequences of a flow diagram attached herein may be carried out by computer program instructions. Thus, a non-transitory computer-readable recording medium can store a program causing a computer to perform the respective steps of a multi-stage menu selection method of the present disclosure. Since the computer program instructions may be loaded in processors of a general purpose computer, a special purpose computer, or other programmable data processing apparatus, the instructions, carried out by the processor of the computer or other programmable data processing apparatus, create means for performing functions described in the respective sequences of the sequence diagram. Since the computer program instructions, in order to implement functions in specific manner, may be stored in a memory useable or readable by a computer or a computer aiming for other programmable data processing apparatus, the instruction stored in the memory useable or readable by a computer may produce manufacturing items including an instruction means for performing functions described in the respective sequences of the sequence diagram. Since the computer program instructions may be loaded in a computer or other programmable data processing apparatus, instructions, a series of sequences of which is executed in a computer or other programmable data processing apparatus to create processes executed by a computer to operate a computer or other programmable data processing apparatus, may provide operations for executing functions described in the respective sequences of the flow diagram.

Moreover, the respective sequences may indicate some of modules, segments, or codes including at least one executable instruction for executing a specific logical function (s). In some alternative embodiments, it is noted that the functions described in the sequences may run out of order. For example, two consecutive sequences may be substantially executed simultaneously or often in reverse order according to corresponding functions.

The explanation as set forth above is merely described a technical idea of the exemplary embodiments of the present invention, and it will be understood by those skilled in the art to which this invention belongs that various changes and modifications may be made without departing from the scope of the essential characteristics of the embodiments of the present invention. Therefore, the exemplary embodiments disclosed herein are not used to limit the technical idea of the present invention, but to explain the present invention, and the scope of the technical idea of the present invention is not limited to these embodiments. Therefore, the scope of protection of the present invention should be construed as defined in the following claims and changes, modifications and equivalents that fall within the technical idea of the present invention are intended to be embraced by the scope of the claims of the present invention.

What is claimed is:

1. An exercise information management apparatus, comprising:
   an information acquiring unit to be mounted on an exercise instrument used for exercise performed by a user and configured to generate exercise instrument information including compensated weight information of a movable portion of the exercise instrument which moves by a force exerted by the user;
   a processor configured to obtain the exercise instrument information from the information acquiring unit and to generate, based on the exercise instrument information and computer executable instructions stored in a non-transitory computer-readable medium, user exercise information including time-series information regarding a use of the exercise instrument by the user,
   wherein the information acquiring unit comprises a pressure sensor which is mounted on the movable portion of the exercise instrument to measure a pressure exerted thereon upon movement of the movable portion of the exercise instrument by the force exerted by the user, and
   wherein the information acquiring unit further comprises an acceleration sensor which is mounted on the movable portion of the exercise instrument to measure an acceleration of the movable portion of the exercise instrument, the information acquiring unit being configured to compensate a value of the pressure using a value of the acceleration so as to generate the compensated weight information and to supply the compensated weight information to the processor for use in generating the user exercise information, and
   an output unit for providing the user exercise information to the user.

2. The exercise information management apparatus of claim 1, wherein the processor is disposed in a portable electronic device of the user, and
   the information acquiring unit comprises a wireless communication module for transmitting the exercise instrument information to the processor.

3. The exercise information management apparatus of claim 2, wherein the exercise information management apparatus further comprises an information storing unit which stores type information on a type of the exercise instrument on which the information acquiring unit is to be mounted,
   the information acquiring unit is configured to obtain the type information from the information storing unit and to generate an exercise instrument recognition signal determined based on the type information and transmit the exercise instrument recognition signal to the processor, and
   the processor is configured to recognize, based on the exercise instrument recognition signal, the type of the exercise instrument used by the user.

4. The exercise information management apparatus of claim 1, wherein the processor is configured to recognize a type of the exercise instrument based on a result of a comparison of the exercise instrument information with predetermined reference exercise instrument information.

5. The exercise information management apparatus of claim 1, wherein the user exercise information includes at least one of type information of the exercise instrument, the compensated weight information corresponding to each type of the exercise instrument, and information on a time period or number of times of the use of the exercise instrument by the user.

6. An exercise information management method performed by an exercise information management apparatus including an information acquiring unit and an information processing unit, comprising:
   after mounting the information acquiring unit, including a pressure sensor and an acceleration sensor, on a movable portion of an exercise instrument which moves by a force exerted by a user during an exercise: generating, using the information acquiring unit mounted on the movable portion of the exercise instrument, exercise instrument information including compensated weight information of the movable portion of the exercise instrument; and
   the information processing unit obtaining the exercise instrument information from the information acquiring unit and generating, based on the exercise instrument information, user exercise information including time-series information regarding a use of the exercise instrument by the user,
   wherein the pressure sensor measures a pressure exerted thereon by the movable portion of the exercise instrument and an acceleration sensor which measures an acceleration of the movable portion of the exercise instrument,
   wherein generating the exercise instrument information comprises generating the compensated weight information based on a value of the pressure and compensating the value of the pressure using a value of the acceleration, and
   wherein the information acquiring unit transmits the compensated weight information to the information processing unit to execute an exercise management function for the user based on the compensated weight information by providing the user exercise information to the user through an output unit.

7. The exercise information management method of claim 6, wherein the information processing unit is disposed in a portable electronic device of the user, and
   the information acquiring unit comprises wireless communication module for transmitting the exercise instrument information to the information processing unit.

8. The exercise information management method of claim 7, wherein the exercise information management apparatus further comprises an information storing unit which stores type information on a type of the exercise instrument on which the information acquiring unit is to be mounted, the exercise information management method further comprising:
   generating an exercise instrument recognition signal determined based on the type information, and
   recognizing, based on the exercise instrument recognition signal, the type of the exercise instrument used by the user.

9. The exercise information management method of claim 6 further comprising determining whether the movable portion of the exercise instrument moves in the exercise instrument using the value of the acceleration measured by the acceleration sensor.

10. The exercise information management method of claim 6 further comprising recognizing a type of the exercise instrument based on a result of a comparison of the exercise instrument information with predetermined reference exercise instrument information.

11. The exercise information management method of claim 6, wherein the user exercise information includes at least one of type information of the exercise instrument, the compensated weight information corresponding to each type of the exercise instrument, and information on a time period or number of times of the use of the exercise instrument by the user.

12. A non-transitory computer-readable storage medium including computer executable instructions, which when executed by a processor, cause the processor to perform an exercise information management method, the exercise information management method comprising:

after mounting an information acquiring unit including a pressure sensor and an acceleration sensor on a movable portion of an exercise instrument which moves by a force exerted by a user during an exercise:

generating, using the information acquiring unit mounted on the movable portion of the exercise instrument, exercise instrument information including compensated weight information of the movable portion of the exercise instrument; and an information processing unit obtaining the exercise instrument information from the information acquiring unit and generating, based on the exercise instrument information, user exercise information including time-series information regarding a use of the exercise instrument by the user, wherein the pressure sensor measures a pressure exerted thereon by the movable portion of the exercise instrument and an acceleration sensor which measures an acceleration of the movable portion of the exercise instrument, wherein the generating the exercise information comprises generating the compensated weight information based on a value of the pressure and compensating the value of the pressure using a value of the acceleration, and wherein the information acquiring unit transmits the compensated weight information to the information processing unit to execute an exercise management function for the user based on the compensated weight information by providing the user exercise information to the user through an output unit.

\* \* \* \* \*